(12) United States Patent
Dickhans et al.

(10) Patent No.: US 9,867,665 B2
(45) Date of Patent: Jan. 16, 2018

(54) MICROWAVE ABLATION CATHETER, HANDLE, AND SYSTEM

(71) Applicant: COVIDIEN LP, Mansfield, MA (US)

(72) Inventors: William J. Dickhans, Longmont, CO (US); Carol L. Shaffer, Plymouth, MN (US); Alex A. Peterson, Maple Grove, MN (US); Arlen J. Reschke, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 675 days.

(21) Appl. No.: 14/479,482

(22) Filed: Sep. 8, 2014

(65) Prior Publication Data

US 2015/0073407 A1 Mar. 12, 2015

Related U.S. Application Data

(60) Provisional application No. 61/874,881, filed on Sep. 6, 2013, provisional application No. 61/974,611, filed
(Continued)

(51) Int. Cl.
*A61B 1/00* (2006.01)
*A61B 18/18* (2006.01)
(Continued)

(52) U.S. Cl.
CPC ...... *A61B 18/1815* (2013.01); *A61B 1/00133* (2013.01); *A61B 1/2676* (2013.01);
(Continued)

(58) Field of Classification Search
CPC .......... A61B 1/00121–1/00135; A61B 1/2676
See application file for complete search history.

(56) References Cited

U.S. PATENT DOCUMENTS

D223,367 S 4/1972 Kountz
D263,020 S 2/1982 Rau, III
(Continued)

FOREIGN PATENT DOCUMENTS

CN 1103807 A 6/1995
CN 102970945 A 3/2013
(Continued)

OTHER PUBLICATIONS

International Search Report dated Dec. 11, 2014 issued in PCT/US2014/054511.
(Continued)

*Primary Examiner* — Scott Getzow

(57) ABSTRACT

A handle for longitudinal movement of a first tubular member over a second tubular member includes a handle body, a nose cone, a locking mechanism, and a retraction control. The nose cone has a sleeve and an outer wall that define a control channel therebetween. The nose cone is moveable over the handle body between extended and retracted positions. The locking mechanism has locked and unlocked positions for selectively fixing the nose cone in the extended and retracted positions. A finger of the retraction control is positioned within the control channel of the nose cone. The retraction control has first and second positions relative to the nose cone for transitioning the locking mechanism between the locked and unlocked position and for moving the nose cone between the extended and retracted positions.

16 Claims, 19 Drawing Sheets

Related U.S. Application Data on Apr. 3, 2014, provisional application No. 62/041,424, filed on Aug. 25, 2014.

(51) Int. Cl.
*A61B 1/267* (2006.01)
*A61B 18/00* (2006.01)
*A61B 90/50* (2016.01)

(52) U.S. Cl.
CPC ..... *A61B 90/50* (2016.02); *A61B 2018/00023* (2013.01); *A61B 2018/00577* (2013.01); *A61B 2018/00982* (2013.01); *A61B 2018/1861* (2013.01); *Y10T 29/49826* (2015.01)

(56) References Cited

U.S. PATENT DOCUMENTS

| | | |
|---|---|---|
| D266,842 S | 11/1982 | Villers et al. |
| D278,306 S | 4/1985 | McIntosh |
| D295,893 S | 5/1988 | Sharkany et al. |
| D295,894 S | 5/1988 | Sharkany et al. |
| 5,244,462 A | 9/1993 | Delahuerga et al. |
| D354,218 S | 1/1995 | Van de Peer |
| 5,569,289 A | 10/1996 | Yoon |
| D424,693 S | 5/2000 | Pruter |
| D424,694 S | 5/2000 | Tetzlaff et al. |
| D425,201 S | 5/2000 | Tetzlaff et al. |
| D449,886 S | 10/2001 | Tetzlaff et al. |
| D457,958 S | 5/2002 | Dycus et al. |
| D457,959 S | 5/2002 | Tetzlaff et al. |
| D487,039 S | 2/2004 | Webster et al. |
| D496,997 S | 10/2004 | Dycus et al. |
| D499,181 S | 11/2004 | Dycus et al. |
| 6,821,282 B2 | 11/2004 | Perry et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| 7,270,656 B2 | 9/2007 | Gowda et al. |
| D564,662 S | 3/2008 | Moses et al. |
| D576,932 S | 9/2008 | Strehler |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| D634,010 S | 3/2011 | DeCarlo |
| 7,942,871 B2 | 5/2011 | Thapliyal et al. |
| 8,157,799 B2 | 4/2012 | Desinger et al. |
| 8,357,193 B2 | 1/2013 | Phan et al. |
| D681,810 S | 5/2013 | Decarlo |
| 8,728,068 B2 | 5/2014 | Nye et al. |
| 2005/0245920 A1 | 11/2005 | Vitullo et al. |
| 2009/0118727 A1 | 5/2009 | Pearson et al. |
| 2009/0299352 A1 | 12/2009 | Zerfas et al. |
| 2010/0280495 A1 | 11/2010 | Paul et al. |
| 2012/0238806 A1 | 9/2012 | Mangiardi et al. |
| 2012/0289772 A1* | 11/2012 | O'Connell ......... A61B 1/00087 600/104 |
| 2013/0023729 A1 | 1/2013 | Vazales et al. |
| 2013/0030249 A1 | 1/2013 | Vazales et al. |
| 2013/0046297 A1 | 2/2013 | Lingeman et al. |
| 2013/0060240 A1 | 3/2013 | Scheller et al. |
| 2013/0123757 A1 | 5/2013 | Crisostomo et al. |
| 2013/0123898 A1 | 5/2013 | Tung et al. |
| 2013/0123912 A1 | 5/2013 | Tung et al. |
| 2013/0144276 A1 | 6/2013 | Crisostomo et al. |
| 2013/0158655 A1 | 6/2013 | Sutton et al. |
| 2013/0231557 A1 | 9/2013 | Li et al. |
| 2014/0046174 A1* | 2/2014 | Ladtkow ............ A61B 1/018 600/424 |
| 2014/0081308 A1 | 3/2014 | Wondka et al. |
| 2014/0114125 A1 | 4/2014 | Scopton et al. |
| 2014/0276033 A1 | 9/2014 | Brannan et al. |

FOREIGN PATENT DOCUMENTS

| | | |
|---|---|---|
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10217281 A1 | 10/2003 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1 159 926 A2 | 12/2001 |
| EP | 1929956 A2 | 6/2008 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 56-161636 | 12/1981 |
| JP | 59-58933 | 4/1984 |
| JP | 5-5106 | 1/1993 |
| JP | 5-08933 | 2/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 9117456 | 5/1997 |

(56) References Cited

FOREIGN PATENT DOCUMENTS

| | | |
|---|---|---|
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2002253569 A | 9/2002 |
| JP | 2004097537 A | 4/2004 |
| JP | 2005522274 A | 7/2005 |
| JP | 2006305361 A | 11/2006 |
| JP | 2008142467 A | 6/2008 |
| KR | 20070093068 A | 9/2007 |
| KR | 20100014406 A | 2/2010 |
| KR | 20120055063 A | 5/2012 |
| SU | 166452 | 11/1964 |
| SU | 401367 A1 | 10/1973 |
| SU | 727201 A2 | 4/1980 |
| WO | 00/36985 A2 | 6/2000 |
| WO | 2008125910 A2 | 10/2008 |
| WO | 2010/035831 A1 | 4/2010 |
| WO | 2011062035 A | 3/2011 |
| WO | 2016033090 A1 | 3/2016 |

OTHER PUBLICATIONS

LigaSureTM Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences-Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Stagegaard, N., Petersen H.H., Chen X., Svendsen J.H., "Indication of the Radiofrequency Induced Lesion Size by Pre-ablation Measurements" Europace (2005) 7, 525-534.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.-Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.

(56) References Cited

OTHER PUBLICATIONS

Vallfors et al., "Automatically Controlled Bipolar Electrocoagulation—'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098, filed Oct. 14, 1993; Roger A. Stern.
U.S. Appl. No. 08/483,742, filed Jun. 7, 1995; Roger A. Stern.
U.S. Appl. No. 14/011,414, filed Aug. 27, 2013; inventor: Ohri.
U.S. Appl. No. 14/011,438, filed Aug. 27, 2013; inventor: Ohri.
Luo Xiongbiao et al., "Beyond Current Guided Bronchoscopy: A Robust and Real-Time Bronchoscopic Ultrasound Navigation System", In: "Lecture Notes in Computer Science (LNCS): Medical Image Computing and Computer-Assisted Intervention—MCCAI 2013", Sep. 22, 2013, vol. 8149, pp. 388-395, XP047041936.
Yehuda Schwarz: "Electromagnetic Navigation", Clinics in Chest Medicine, vol. 31, No. 1, Mar. 1, 2010, pp. 65-73, XP055131118.
F.J.F. Herth: "Bronchoscopic Techniques in Diagnosis and Staging of Lung Cancer", Breathe, vol. 7, No. 4, Jun. 1, 2011, pp. 324-337, XP055358488.
William Krimsky et al: "Bronchoscopy and the Peripheral Nodule in the Age of Lung Cancer Screening and Targeting Therapies", Current Respiratory Care Reports, vol. 1, No. 1, Jan. 25, 2012, pp. 67-71, XP055358485.
European Search Report dated Apr. 11, 2017, issued in EP Application No. 14842294.
European Search Report dated Apr. 12, 2017, issued in EP Application No. 14842874.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.

Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-LInear Thermal Transport in Biological Media", Proc. ASME HTD-355, 131 (1997).

(56) References Cited

OTHER PUBLICATIONS

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
U.S. Appl. No. 14/242,019, filed Apr. 1, 2014; inventor: Brannan.
U.S. Appl. No. 14/242,048, filed Apr. 1, 2014; inventor: Prakash.
U.S. Appl. No. 14/281,264, filed May 19, 2014; inventor: Prakash.
U.S. Appl. No. 14/281,344, filed May 19, 2014; inventor: Shiu.
U.S. Appl. No. 14/300,824, filed Jun. 10, 2014; inventor: Behnke.
U.S. Appl. No. 14/300,871, filed Jun. 10, 2014; inventor: Bonn.
U.S. Appl. No. 14/306,865, filed Jun. 17, 2014; inventor: Brannan.
U.S. Appl. No. 62/020,240, filed Jul. 2, 2014, inventor Andrew Brown.
Japanese Office Action dated Jun. 20, 2017, issued in JP Application No. 2016540341.
Supplemental European Search Report dated Jun. 26, 2017, issued in EP Application No. 14843010.
Japan Electronics and Information Technology Industries Association, Kaitei Iyou Choonpa Kiki Handobuku, Japan, Corona, Jan. 20, 1997, p. 15, p. 35. (A part or the whole of the non patent literature indicated above may not be forwarded due to restrictions arising from law or contract.).
Chinese Office Action dated Aug. 18, 2017, issued in CN Application No. 201480057462.

\* cited by examiner

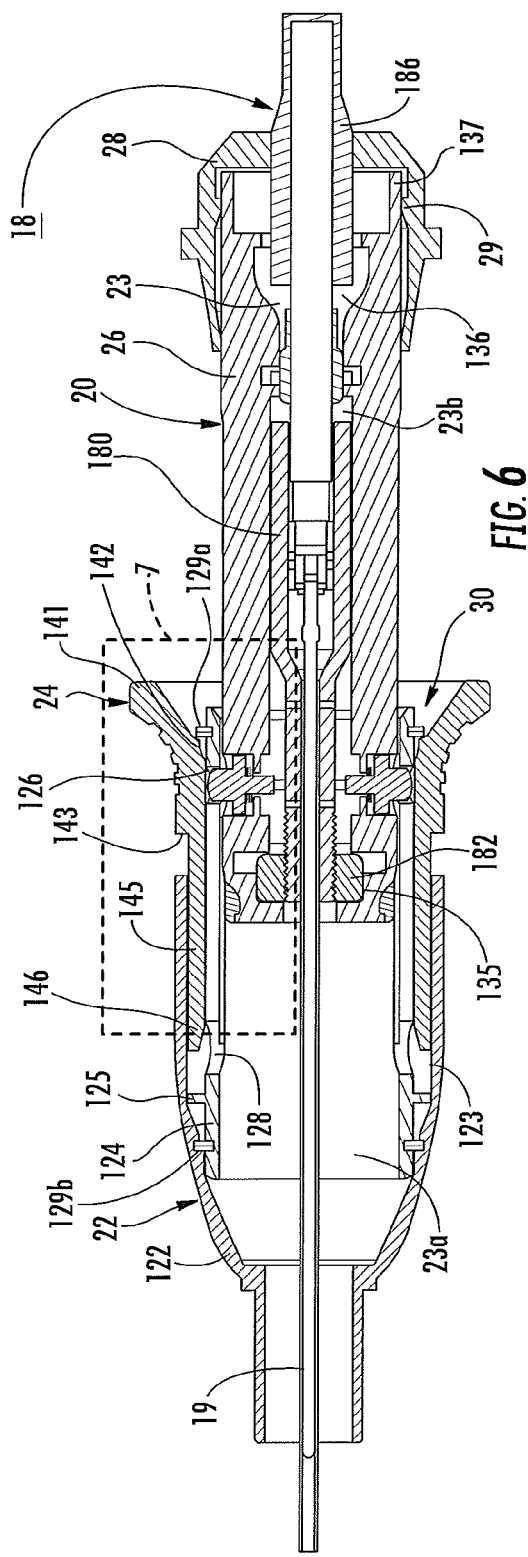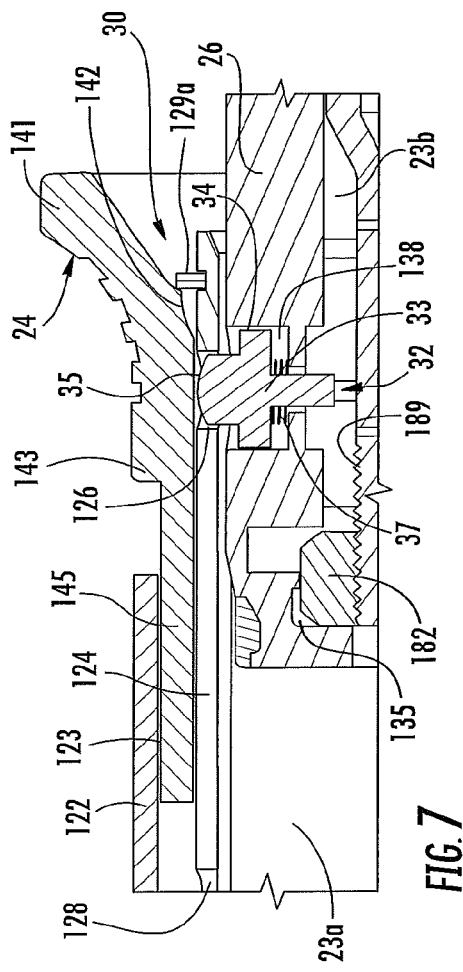
FIG. 6
FIG. 7

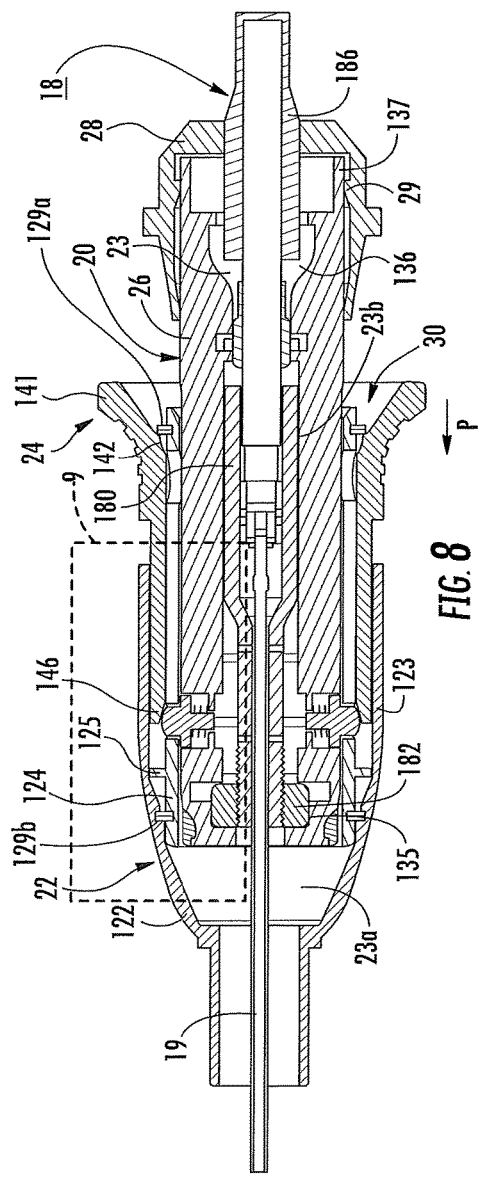
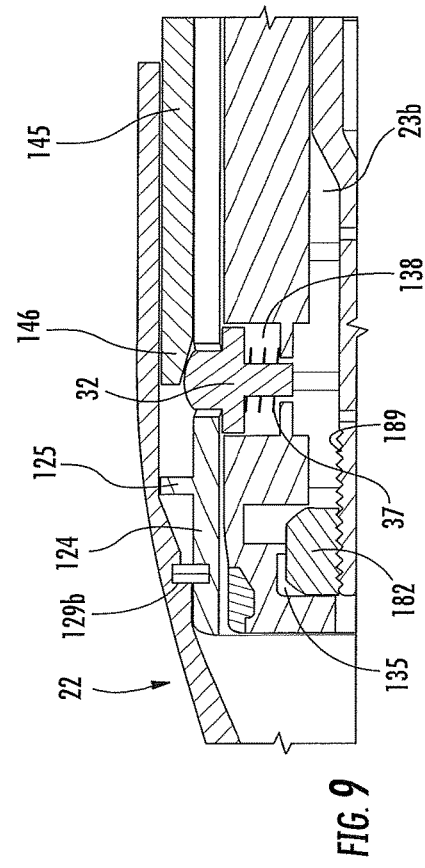
FIG. 8
FIG. 9

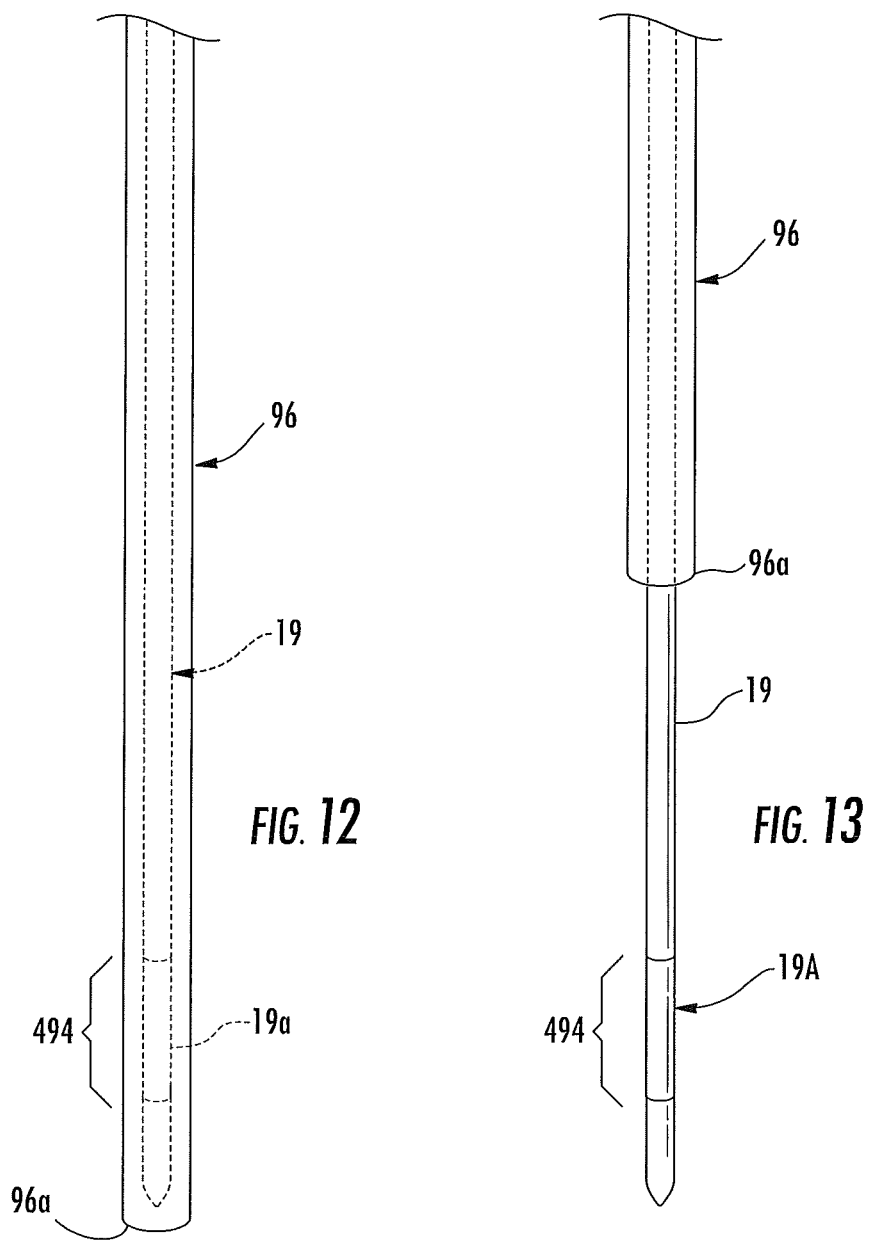

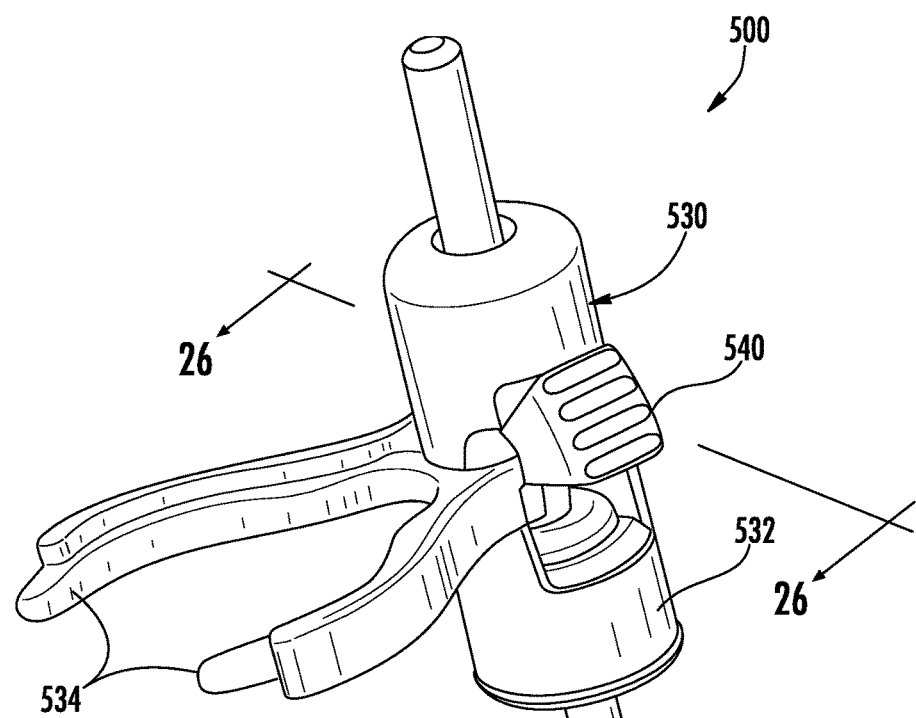
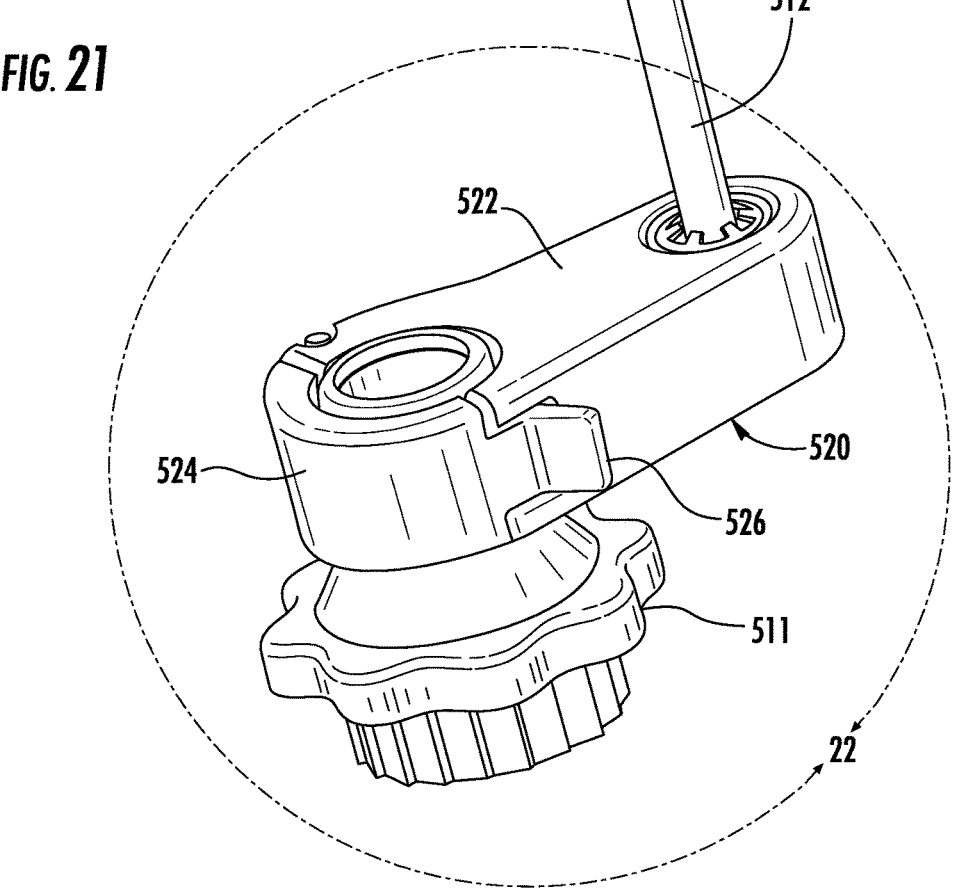
FIG. 21

MICROWAVE ABLATION CATHETER, HANDLE, AND SYSTEM

CROSS-REFERENCE TO RELATED APPLICATIONS

This application claims the benefit of, and priority to, U.S. Provisional Patent Application Ser. No. 61/874,881, filed on Sep. 6, 2013; U.S. Provisional Patent Application No. 61/974,611, filed on Apr. 3, 2014; and U.S. Provisional Patent Application No. 62/041,424, filed on Aug. 25, 2014. The entire contents of each of the above applications are hereby incorporated herein by reference. This application is related to U.S. patent application Ser. No. 14/479,502, filed on Sep. 8, 2014.

BACKGROUND

1. Technical Field

The present disclosure relates to surgical instruments and, more specifically, to handles for moving an outer tubular member relative to an inner tubular member inserted therethrough.

2. Discussion of Related Art

A common interventional procedure in the field of pulmonary medicine is bronchoscopy, in which a bronchoscope is inserted into the airways through the patient's nose or mouth. The structure of a bronchoscope generally includes a long, thin, flexible tube that typically contains three elements: an illumination assembly for illuminating the region distal to the bronchoscope's tip via an optical fiber connected to an external light source; an imaging assembly for delivering back a video image from the bronchoscope's distal tip; and a lumen or working channel through which instruments may be inserted, including but not limited to placement (e.g., guide wires), diagnostic (e.g., biopsy tools) and therapeutic (e.g., treatment catheters or laser, cryogenic, radio frequency, or microwave tissue treatment probes) instruments. The distal tip of a bronchoscope is steerable. Rotating a lever placed at the handle of the bronchoscope actuates a steering mechanism that deflects the tip in one or more directions.

Bronchoscopies are performed by pulmonologists, also known as bronchoscopists, and are used routinely in the diagnosis and treatment of conditions such as lung cancer, airway stenosis, and emphysema. Bronchoscopies are typically performed by a staff of at least two persons: the bronchoscopist and at least one assistant, usually a nurse. During a typical procedure, the bronchoscopist holds the bronchoscope handle with one hand and the bronchoscope tube with the other hand. The bronchoscopist manipulates the distal tip of the bronchoscope inside the lung by rotating a deflection lever and by pushing and pulling the tube. Once the tip is brought to a target, an instrument can be inserted into the working channel to perform a diagnostic or therapeutic procedure.

During insertion and operation of the instruments, the distal tip of the bronchoscope should be held steady at the target. Two hands are needed to secure the bronchoscope in place and one to two more hands are needed for inserting and actuating the instrument. Generally, the bronchoscopist releases the bronchoscope to insert and actuate the instrument. Performing a procedure that requires two people is generally more expensive and the potential for error is increased. Hence, it is desirable to modify a procedure so that it may be performed with one or two hands, if possible.

Additionally, because all of the instruments used with a bronchoscope are necessarily long and slender, the instruments do not retain shape when unsupported. Thus, inserting an instrument into a bronchoscope can be difficult or impossible to do quickly with one hand. While this problem can be addressed easily by holding the end of the sheath in one hand and the instrument in another, this would again require additional free hands during performance of the procedure.

During particular procedures (e.g., microwave ablation and biopsy) a catheter or extended working channel may be inserted through a working channel to enable navigation to sites too remote and having luminal diameters too small for the bronchoscope. An instrument may be inserted through the catheter or extended working channel in order to perform a biopsy or ablation procedure. Current systems and methodologies for extending the surgical instrument from the catheter or retracting the catheter from the placement of the surgical instrument require at least two people to manipulate all the elements of the system including the bronchoscope.

Accordingly, there is a need for an apparatus that would facilitate one-handed actuation of the catheter and surgical instrument leaving one hand to manipulate the bronchoscope. In addition, there is a need for a support for use with a bronchoscope that would facilitate operation of a bronchoscope and associated tools by a single practitioner. It would also be advantageous to provide a support for the probe and the catheter to allow a single practitioner to manipulate a catheter, a probe, and a bronchoscope during the procedure.

SUMMARY

In an aspect of the present disclosure, a handle for longitudinal movement of a first tubular member over a second tubular member includes a handle body, a nose cone, a locking mechanism, and a retraction control. The nose cone has a sleeve and an outer wall defining a control channel therebetween. The nose cone is moveable over the handle body between extended and retracted positions. The locking mechanism has locked and unlocked positions for selectively fixing the nose cone in the extended and retracted positions. The retraction control includes a finger positioned within the control channel of the nose cone and has first and second positions relative to the nose cone for transitioning the locking mechanism between the locked and unlocked positions and for moving the nose cone between the extended and retracted positions.

In aspects, when the nose cone is in the extended position and the retraction control is in the first position, the locking mechanism is in the locked position to fix the nose cone in the extended position.

In some aspects, when the nose cone is in the extended position and the retraction control is in the second position, the locking mechanism is in the unlocked position such that the nose cone is moveable relative to the handle body. When the nose cone reaches the retracted position, the locking mechanism transitions to the locked position to fix the nose cone in the retracted position.

In certain aspects, when the nose cone is in the retracted position and the retraction control is in the second position, the locking mechanism is in the locked position to fix the nose cone in the extended position.

In particular aspects, when the nose cone is in the retracted position and the retraction control is in the first position, the locking mechanism is in the unlocked position such that the nose cone is moveable relative to the handle body. When the nose cone reaches the extended position, the locking mechanism may transition to the locked position to fix the nose cone in the extended position.

In aspects, the second position of the retraction control is proximal to the first position of the retraction control. The locking mechanism may be disposed within a slot defined in the housing body. The locking mechanism may include a locking pin that has a retention plate. The locking pin may be biased out of the slot defined in the housing body such that the retention plate retains the locking pin within the slot. The sleeve of the nose cone may define first and second openings such that when the nose cone is in the extended position and the locking pin is in the locked position, the locking pin is disposed within the first opening. In addition, when the nose cone is in the retracted position and the locking pin is in the locked position, the locking pin may be disposed within the second opening.

In another aspect of the present disclosure, a surgical system includes an extended working channel having proximal and distal ends, a handle defining a through passage, a retraction control, and a catheter assembly disposed within the through passage of the handle. The handle includes a housing body defining a proximal portion of the through passage, a nose cone coupled to the proximal end of the extended working channel, a locking mechanism, and a retraction control. The nose cone has a sleeve and an outer wall defining a control channel therebetween. The nose cone defines a distal portion of the through passage in communication with the extended working channel. The nose cone is longitudinally moveable over the housing body between extended and retracted positions. The locking mechanism has locked and unlocked positions for selectively fixing the nose cone in the extended and retracted positions. The retraction control includes a finger positioned within the control channel of the nose cone. The retraction control has first and second positions relative to the nose cone for transitioning the locking mechanism between the locked and unlocked positions and for moving the nose cone between the extended and retracted positions. The catheter assembly includes a catheter hub positioned within the proximal portion of the through passage and an ablation probe extending from the catheter hub through the nose cone of the handle and through the extended working channel. The ablation probe has a distal end that is disposed within the extended working channel when the handle is in the extend position and that is position positioned distal to the distal end of the extended working channel when the handle is in the retracted position.

In aspects, the catheter hub combines coolant tubes and an antenna into the ablation probe. The catheter hub may include an adjustment nut that is positioned over an outer surface of the catheter hub. The housing portion may define a nut recess for receiving the adjustment nut to longitudinally fix the ablation probe to the housing portion. The adjustment nut is threaded to cooperate with threads on the outer surface of the catheter hub to allow fine adjustment of the length of the ablation probe relative to the housing portion. The distal end of the ablation probe may be positioned within the distal end of the extended working channel when the nose cone is in the extended position. The distal end of the ablation probe may be positioned distal to the distal end of the extended working channel when the nose cone is in the retracted position.

In another aspect of the present disclosure, a method of assembly of a surgical system includes positioning a catheter assembly within a half of a first portion of a passage defined within a first half of a housing body of a handle, securing a second half of the housing body of the handle to the first half of the housing body with the catheter assembly that is positioned in a half of the first portion of the passage defined within the second half of the housing body to form the housing body, sliding a nose cone of the handle over a distal portion of the housing body, and inserting a finger of a retraction control within a control channel defined between a sleeve and outer wall of the nose cone. The nose cone defines a second portion of the passage that receives a probe of the catheter assembly therethrough.

In aspects, the positioning of the catheter assembly within the first half of the first portion of the passage that is defined within the first half of the housing body includes position an adjustment nut within a nut recess defined in the housing body to adjust the length of the probe extending distally from the housing body. The method may further include rotating the adjustment nut about a threaded portion of the catheter hub to fix the length of the probe that extends distally from the housing body. Securing the second half of the housing body to the first half of the housing body may prevent adjustment of the length of the probe extending distally from the housing body during use of the surgical system.

In another aspect of the present disclosure, a support system includes a rail, a lower support, and an instrument support. The rail has upper and lower ends that define a longitudinal axis therebetween. The lower support is configured to receive a portion of a bronchoscope and to selectively fix the bronchoscope relative to the rail. The instrument support is slidably disposed on the rail and is selectively lockable to the rail. The instrument support is configured to releasably couple to a surgical instrument inserted through the bronchoscope to fix the position of a portion of the surgical instrument relative to the bronchoscope.

In aspects, the instrument support includes a clamp arm and a clamp arm collar. The clamp arm collar may be slidably disposed over the rail. The clamp arm may include instrument fingers that extend from the clamp arm collar. The instrument fingers may define an instrument passage that is configured to releasably couple to the surgical instrument. The instrument support may include a locking arm that has a locking cam. The clamp arm collar may include a camming surface and the locking cam may be configured to compress the camming surface of the clamp arm collar against the rail when the locking arm is in the locked position to lock the instrument support to the rail. In the locked position, the instrument support may be radially locked relative to the rail.

In some aspects, the lower support defines a rail opening that is configured to receive the lower end of the rail. The support system may include a collar positioned within the rail opening that includes a threaded portion. The support system may include a securement member that is threaded over the threaded portion of the collar to compress the collar over the lower end of the rail to fix the rail to the lower support.

In certain aspects, the lower support includes a pair of support fingers that extend orthogonally from the rail. The support fingers may define a support opening therebetween. The support fingers may be configured to compress the support opening about the bronchoscope to fix the lower support relative to the bronchoscope.

In another aspect of the present disclosure, a surgical system includes a bronchoscope, an extended working channel that extends through the bronchoscope, an elongated surgical instrument that is inserted through the extended working channel, and a support system for supporting the elongated surgical instrument relative to the bronchoscope. The support system includes a rail, a lower support, and an instrument support. The rail has upper and lower ends that define a longitudinal axis therebetween. The lower support is fixed to the lower end of the rail and to the bronchoscope to fix the rail to the bronchoscope. The instrument support is slidably disposed on the rail and is selectively lockable to the rail. The instrument support is releasably coupled to a first portion of the elongated surgical instrument to fix the position of the first portion of the elongated surgical instrument relative to the bronchoscope.

In aspects, a second portion of the elongated surgical instrument is moveable relative to the bronchoscope. The second portion of the elongated surgical instrument may be fixed to a proximal end of the extended working channel such that the extended working channel is moveable relative to the bronchoscope and the first portion of the elongated surgical instrument. The first portion of the elongated surgical instrument includes an ablation probe that extends through the second portion of the elongated surgical instrument and the extended working channel.

In some aspects, the extended working channel includes a telescopic extended working channel handle that is fixed to the bronchoscope. When the telescopic extended working channel handle is manipulated, the bronchoscope and the elongated surgical instrument that is fixed to the bronchoscope by the support system move in concert with the telescopic extended working channel handle.

In another aspect of the present disclosure, a method of positioning an elongated surgical instrument adjacent targeted tissue includes inserting the elongated surgical instrument into an extended working channel, securing a support system to the bronchoscope, coupling a portion of the elongated surgical instrument to the support system to fix the portion of the elongated surgical instrument to the bronchoscope, and manipulating a portion of the extended working channel such that the bronchoscope, the elongated surgical instrument, and the support system move in concert with the portion of the extended working channel. The elongated surgical instrument may have a locatable guide adjacent a distal end thereof. The extended working channel passes through a bronchoscope positioned in an airway of a patient.

In aspects, manipulating a portion of the extended working channel includes manipulating a telescopic extended working channel handle of the extended working channel that is connected to the bronchoscope.

In some aspects, securing the support system to the bronchoscope may include fixing a lower support of the support system to a portion of the bronchoscope. Securing the support system to the bronchoscope may include inserting a lower end of a rail of the support system into the lower support.

In certain aspects, coupling a portion of the elongated surgical instrument to the support system includes coupling the portion of the elongated surgical instrument in an instrument support of the support system. The method may include locking the instrument support to a rail of the support system to fix the portion of the elongated surgical instrument relative to the bronchoscope.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 3A is a cross-sectional view taken along the section line 3A-3A shown in FIG. 3;

FIG. 6 is a longitudinal cross-sectional view of the retraction handle with the retraction control in a second position and the nose cone in an extended position;

FIG. 7 is an enlarged view of the indicated area of detail of FIG. 6;

FIG. 8 is a longitudinal cross-sectional view of the retraction handle with the retraction control in the second position and the nose cone in the retracted position;

FIG. 9 is an enlarged view of the indicated area of detail of FIG. 8;

FIG. 12 is a perspective view of a distal end of the catheter of FIG. 2;

FIG. 13 is a perspective view of the distal end of the catheter of FIG. 12 when the retraction handle is in the retracted position;

FIG. 15 is a side cross-sectional view of taken along the section line 15-15 of

FIG. 14;

FIG. 21 is a perspective view of another rail system provided in accordance with the present disclosure;

DETAILED DESCRIPTION

Figure 1:
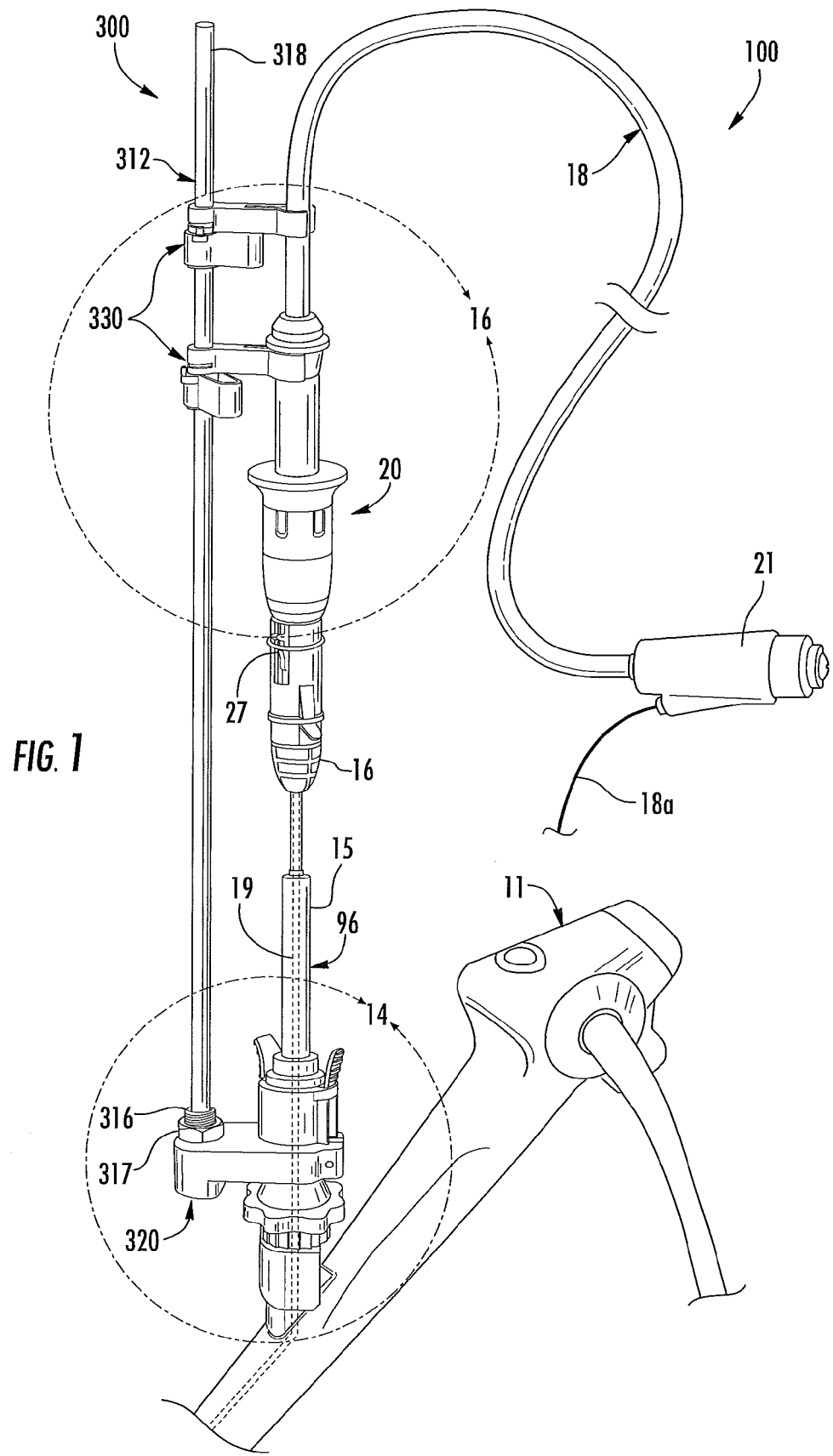
FIG. 1 is a perspective view of an exemplary surgical system including a retraction handle and a rail system in accordance with the present disclosure.

According to aspects of the present disclosure, a support system mounts to a bronchoscope to support instruments inserted through and associated with the bronchoscope. In one embodiment, the support system is configured to separately support a retraction handle and a catheter inserted through the retraction handle and the bronchoscope. The retraction handle is coupled to an extended working channel that passes through the bronchoscope and into the anatomy of a patient. The catheter is inserted through the extended working channel to a position adjacent targeted tissue. When the catheter is positioned adjacent the targeted tissue, the retraction handle is moved to a retracted position to expose the distal end of the catheter adjacent the targeted tissue such that the catheter can treat the targeted tissue. The retraction handle may be moved to the retracted position with one hand of a clinician as detailed herein.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Referring now to FIG. 1, a surgical system 10 includes a bronchoscope 11, a telescopic extended working channel (EWC) handle 15, an ablation catheter assembly 100, including a cable 18, a probe 19, a retraction handle 20, and a connector 21 for connection to an energy source such as a microwave generator (not shown). A portion 18a of the cable 18 may extend from the connector 21 to a coolant source (not shown) for providing a cooling fluid to the ablation catheter assembly 100. FIG. 1 also depicts a rail system 300 including a support rail 312 supported on the bronchoscope 11 by a lower support member 320 and includes a device support 330 that supports the retraction handle 20 as detailed below. The support rail 312 may include an additional a device support 330 that supports the cable 18 above the retraction handle 20. The rail system 300 is disclosed in greater detail below.

The telescopic EWC handle 15 connects to the bronchoscope 11 and is in communication with an EWC 96, formed internally therein, such that instruments passed through the telescopic EWC handle 15 pass through the EWC 96. The proximal end 16 of the telescopic EWC handle 15 includes a mating feature that is engaged by the retraction handle 20. The retraction handle 20 mates with the proximal end 16 of the telescopic EWC handle 15 (FIG. 1) enabling movement of the EWC 96 relative to the ablation probe 19, as described below. The retraction handle 20 may include an engagement feature 27 (FIG. 2) for engaging the mating feature of the proximal end 16 of the telescopic EWC handle 15. The engagement feature 27 may be a clip that is received within an opening defined in the proximal end 16 of the telescopic EWC handle 15.

Figure 2:
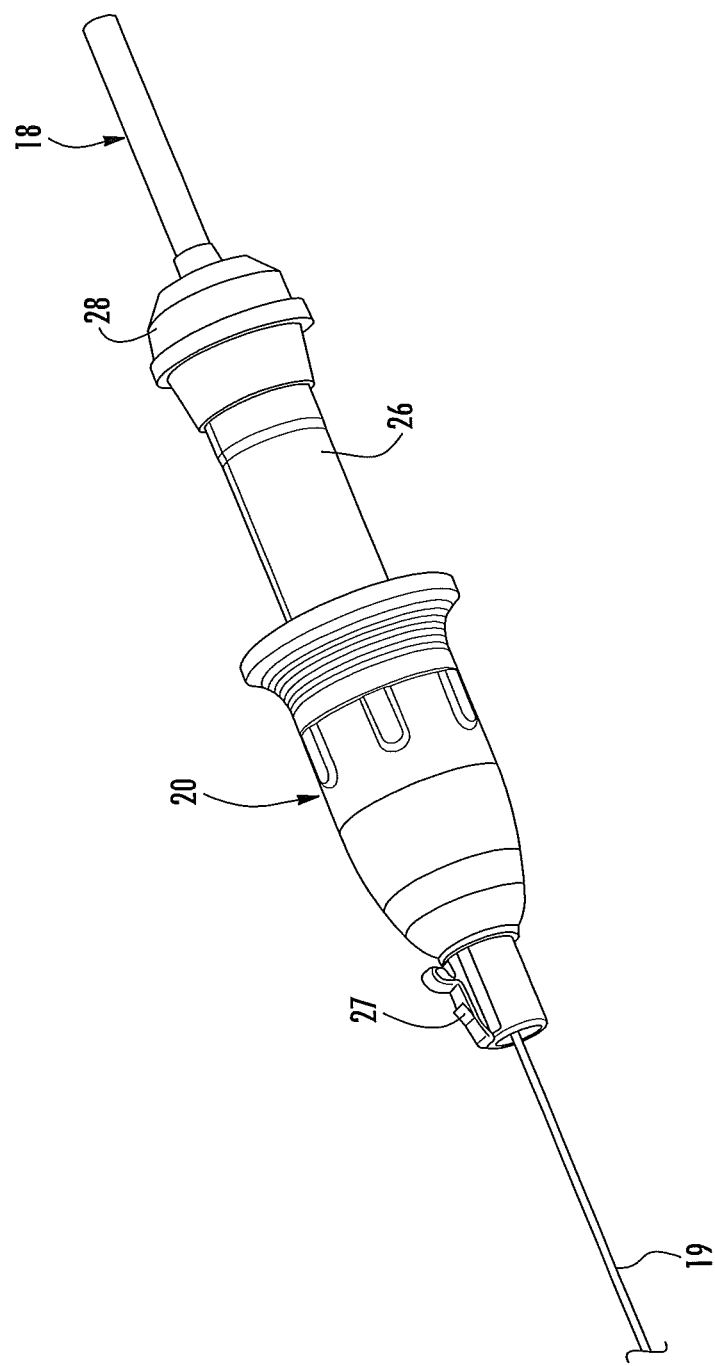
FIG. 2 is a perspective view of the retraction handle of FIG. 1.
Figure 3:
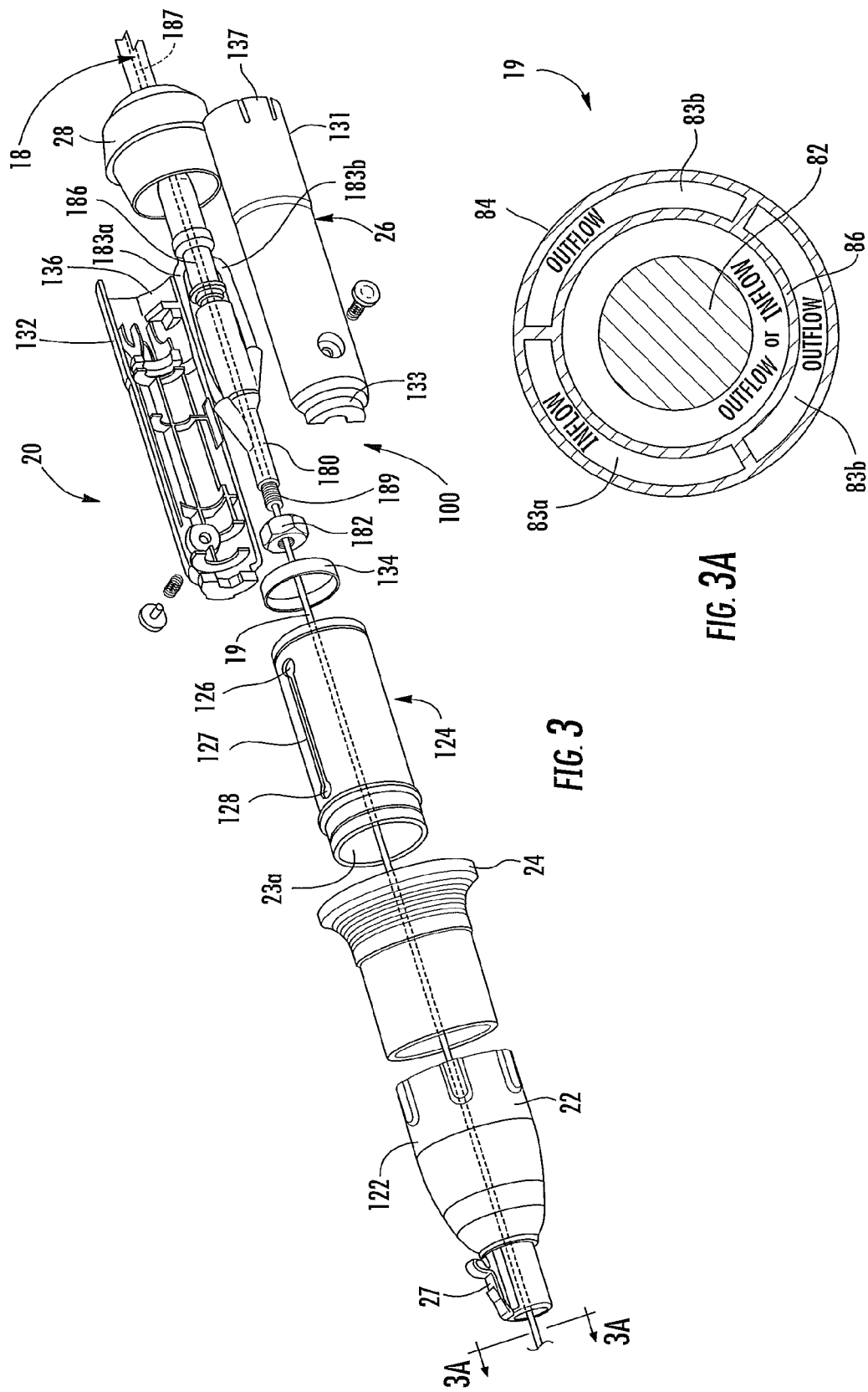
FIG. 3 is an exploded perspective view showing the components of the retraction handle of FIG. 1.

With reference to FIGS. 2 and 3, the ablation catheter assembly 100 includes an ablation probe 19 and a catheter hub 180 positioned within a through passage 23 (FIG. 4) formed in the retraction handle 20. The ablation probe 19 extends distally from the catheter hub 180, through the telescopic EWC handle 15 (FIG. 1) and the EWC 96 formed internal therein, and to a distal end 96a (FIGS. 12 and 13) of the EWC 96. The catheter hub 180 includes coolant channels 183 and a connector 186 enabling electrical connection of cable 18 with an antenna 187, described below. One of the coolant channels 183a is an inflow channel and the other coolant channel 183b is an outflow channel. The coolant channels 183a, 183b, the connector 186, and the antenna 187 are coupled together within the catheter hub 180 into the ablation probe 19.

With particular reference to FIG. 3A, the ablation probe 19 includes a microwave antenna 82 electrically connected to cable 18 and sized be received within an outer sheath 84 of the ablation probe 19. An inner sheath 86 is formed within the outer sheath 84 and surrounds the microwave antenna 82, the inner sheath 86 separates the interior of the ablation probe 19 into inflow and outflow coolant paths 83a and 83b such that coolant flows through the inflow channel 183a, along the microwave antenna 82 in the inflow coolant path 83a to a distal end of the ablation probe 19, and returns via the outflow coolant path 83b separating the inner sheath 86 from the outer sheath 84 to the outflow channel 183b. In this manner the ablation probe 19, and more particularly the microwave antenna 82, is actively cooled. Examples of microwave antenna construction may be found in commonly assigned U.S. patent application Ser. No. 13/835,283 entitled "Microwave Energy-Device and System," and Ser. No. 13/836,519 entitled "Microwave Ablation Catheter and Method of Utilizing Same," the entire contents of each is incorporated herein by reference.

Referring back to FIG. 3, the catheter hub 180 includes a threaded portion 189 adjacent a distal end thereof. The threaded portion 189 receives an adjustment nut 182 that adjusts the length of the ablation probe 19 extending from the retraction handle 20. The adjustment nut 182 may be used by the manufacturer of the retraction handle 20 to finely adjust the length of the ablation probe 19 extending from the retraction handle 20 when the retraction handle 20 is assembled over the cable 18. Such an adjustment mechanism may allow the manufacturer to employ increased tolerances in the length of the ablation probe 19 during manufacture and to finely adjust the length of the ablation probe 19 during assembly. It will be appreciated that once the retraction handle 20 is assembled over the catheter hub 180, the adjustment nut 182 is not accessible by a clinician using the retraction handle 20 (i.e., once the length of the ablation probe 19 is set during assembly, the length of the ablation probe is fixed).

Figure 4:
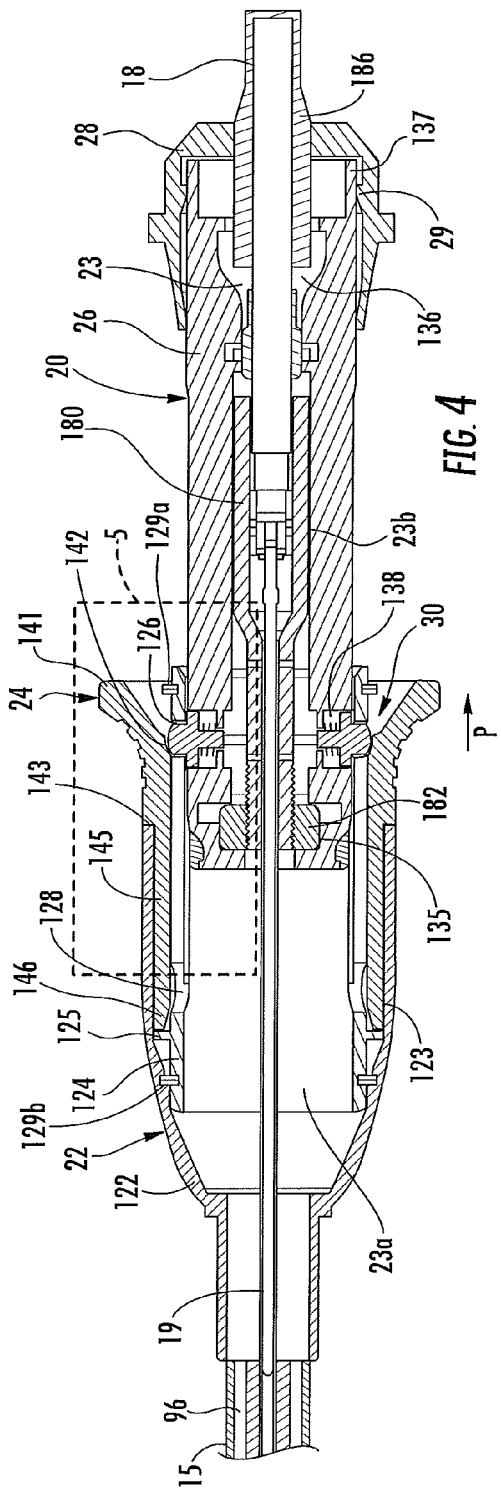
FIG. 4 is a longitudinal cross-sectional view of the retraction handle of FIG. 1 taken along the longitudinal axis thereof.

With additional reference to FIG. 4, the retraction handle 20 includes a nose cone 22, a retraction control 24, a sleeve 124 (FIG. 3), a handle body 26, a spindle cap 28, and a locking mechanism 30. The components of the retraction handle 20 (e.g., the nose cone 22, the retraction control 24, the handle body 26, and the spindle cap 28) may be rotatable relative to one another to allow the components to rotate without applying a rotational force to the cable 18 or the EWC 96.

The handle body 26 includes first and second body sections 131, 132 (FIG. 3) that are secured together to define a second portion 23b (FIG. 4) of the through passage 23 therethrough. As shown in FIG. 3, the distal end of the handle body 26 defines a ring groove 133 in an outer surface thereof that receives a ring 134 that secures the first and second body sections 131, 132 together. The distal end of the handle body 26 is received in the first portion 23*a* of the through passage 23 defined by the nose cone 22. The second portion 23*b* of the through passage 23 defined by the handle body 26 includes a nut recess 135 that is positioned adjacent a distal end thereof and a cable recess 136 that is positioned adjacent a proximal end thereof.

The outer surface of the handle body 26 includes mating tabs 137 positioned at a proximal end thereof. The spindle cap 28 is disposed over the proximal end of the handle body 26 and includes retention tabs 29 that engage the mating tabs 137 of the handle body to secure the spindle cap 28 to the handle body 26 and to secure the proximal end of the first and second body sections 131, 132 together.

Figure 5:
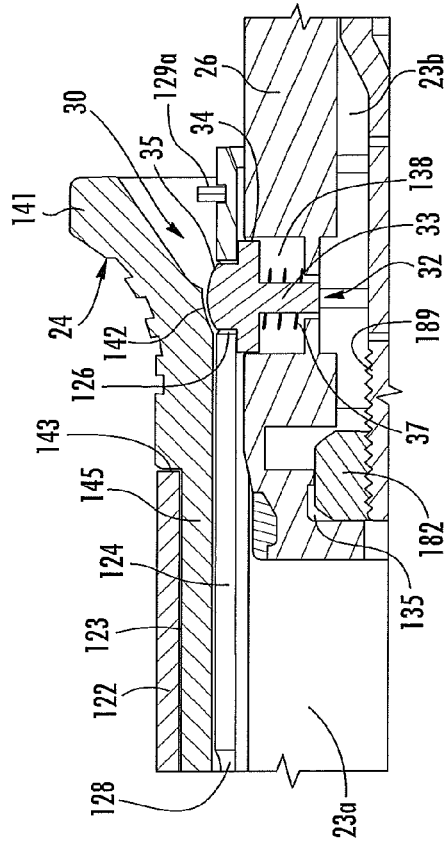
FIG. 5 is an enlarged view of the indicated area of detail of FIG. 4.

Referring to FIGS. 4 and 5, the nose cone 22 defines an outer wall 122 and receives a sleeve 124. The sleeve 124 defines a first portion 23*a* of a through passage 23 that receives the handle body 26 and a portion of the probe 19 therewithin. The outer wall 122 of nose cone 22 and the sleeve 124 define a control channel 123 therebetween that slidably receives the retraction control 24. The distal end of the control channel 123 includes a control stop 125 that may limit the proximal displacement of the retraction control 24 relative to the nose cone 22.

The sleeve 124 includes a first opening 126 and a second opening 128 positioned distal to the first opening 126. The sleeve 124 may optionally define a slot 127 in communication with the first and second openings 126, 128 parallel to the longitudinal axis. The sleeve 124 includes a retention ring 129*a* disposed about the inner wall 124 adjacent a proximal end thereof that prevents the retraction control 24 from disengaging the sleeve 124 of (i.e., sliding proximally off of the sleeve 124). The sleeve 124 is formed separately from the nose cone 22 and joined thereto by a distal retention ring 129*b*. It is also within the scope of this disclosure that the sleeve 124 may be integrally formed with the nose cone 22.

The retraction control 24 includes a proximal flange 141 and a distal finger 145 extending therefrom. The proximal flange 141 includes an inner angled surface 142 and a shoulder 143. The distal finger 145 includes a ramped surface 146 adjacent the inner wall 124 of the nose cone 22. The distal finger 145 is positioned over the inner wall 124 of the nose cone 22 such that the distal finger 145 is disposed substantially between the sleeve 124 and the outer wall 122 of the nose cone 22.

Referring in particular to FIG. 4, a locking mechanism 30 selectively locks the nose cone 22 in each of an extended position and a retracted position as detailed below. The outer surface of the handle body 26 defines pin slots 138 positioned adjacent a distal end thereof which may be positioned proximal to the nut recess 135. The locking mechanism 30 includes a locking pin 32 disposed within each of the pin slots 138 and a pin biasing member 37 supported within each of the pin slots 138 between a respective locking pin 32 and the housing body 26. Each locking pin 32 includes a shaft 33, a retention plate 34, and a locking surface 35 and is disposed substantially within a respective pin slot 138. The shaft 33 may pass through the pin biasing member 37. Each pin biasing member 37 engages the retention plate 34 of a respective locking pin 32 to urge the respective locking pin 32 out of pin slot 138.

The locking pins 32 are moveable between a locked position and an unlocked position. In the locked position, the locking surface 35 of the locking pin 32 protrudes from the pin slot 138 and through one of the first and second openings 126, 128 of the sleeve 124. In the locked position, the retention plate 34 engages the inner surface of the sleeve 124 adjacent one of the first and second openings 126, 128 to prevent the locking pin 32 from passing entirely through the first or second openings 126, 128. In the unlocked position, the locking pin 32 is moved towards the longitudinal axis of the handle 20 against the pin biasing member 37 such that the locking surface 35 of the locking pin 32 is deflected within the inner surface of the sleeve 124. In the unlocked position (FIG. 6), the locking surface 35 of the locking pin 32 is engaged by the inner surface of sleeve 124 between the first and second openings 126, 128.

When the locking pins 32 are in the locked position and positioned to protruded through the first openings 126 (FIGS. 4 and 5), the nose cone 22 is in the extended position. When the locking pins 32 are in the locked position and positioned to protrude through the second openings 128 (FIGS. 7 and 8), the nose cone 22 is in the retracted position. The retraction control 24 engages the locking surface 35 of the locking pins 32 to move the locking pins 32 from the locked position to the unlocked position to permit the nose cone 22 to move between the extended and retracted positions as detailed below.

Referring to FIGS. 4-9, the retraction control 24 moves the nose cone 22 along the longitudinal axis from an extended position (FIG. 4) to a retracted position (FIG. 8). It will be appreciated that the extended and retracted positions refer to the location of the distal end 96*a* of the EWC 96 relative to the distal end 19*a* of the probe 19 as shown in FIGS. 12 and 13. In FIGS. 4 and 12, the EWC 96 is extended beyond the distal end 19*a* of the probe 19, and in FIGS. 5 and 13 the EWC 96 is retracted, exposing the distal end 19*a* of probe 19. In part this orientation of movement is necessary when, as shown in FIG. 1, the housing body 26 of handle 20 is secured to the rail system 300 by device supports 330. The retraction control 24 has a first position (FIG. 4) relative to the nose cone 22 such that the retraction control 24 (i.e., the distal finger 145) is positioned over the second openings 128 formed in the sleeve 124 leaving the first openings 126 unobstructed and a second position (FIG. 6) relative to the nose cone 22 such that the retraction control 24 (i.e., the proximal flange 141) is positioned proximal to the first openings 126 leaving the second openings 128 unobstructed. Initially referring to FIGS. 4 and 5, the nose cone 22 is in the extended position, the retraction control 24 in a first position relative to the nose cone 22, and the locking pins 32 are in the locked position within the first openings 126.

Referring now to FIGS. 6 and 7, the nose cone 22 remains in the extended position and the retraction control 24 is moved to the second position relative to the nose cone 22 that is proximal to the first position. As the retraction control 24 is moved to the second position, the inner angled surface 142 of the proximal flange 141 engages the locking surface 35 of the locking pins 32 to move the locking pins 32 from the locked position to the unlocked position. When the locking pins 32 are in the unlocked position, the nose cone 22 is free to move towards the retracted position (FIG. 8).

With reference to FIGS. 8 and 9, additional retraction of the retraction control 24 stops when the inner angled surface 142 of the retraction control 24 engages retention ring 129*a* fixed to the inner wall 124 stopping the movement of the nose cone 22 proximally over the housing body 26. As the nose cone 22 is retracted, the retraction control 24 remains in the second position relative to the nose cone 22 and the locking surface 35 of the locking pins 32 slide along the inner surface of the sleeve 124 between the first and second openings 126, 128. When the nose cone 22 reaches the retracted position (FIG. 8), the locking surface 35 of the locking pins 32, being urged by the pin biasing members 37, extend through the second openings 128 such that the locking pins 32 are in the locked position to fix the nose cone 22 in the retracted position.

Now with reference to FIGS. 4, 5, and 8-11, the movement of the nose cone 22 from the retracted position (FIG. 8) to the extended position (FIG. 4) will be described in accordance with the present disclosure. Referring initially to FIGS. 8 and 9, the nose cone 22 is in the retracted position, the retraction control 24 is in the second position, and the locking pins 32 are disposed in the locked position within the second openings 128 formed in the sleeve 124.

Figure 10:
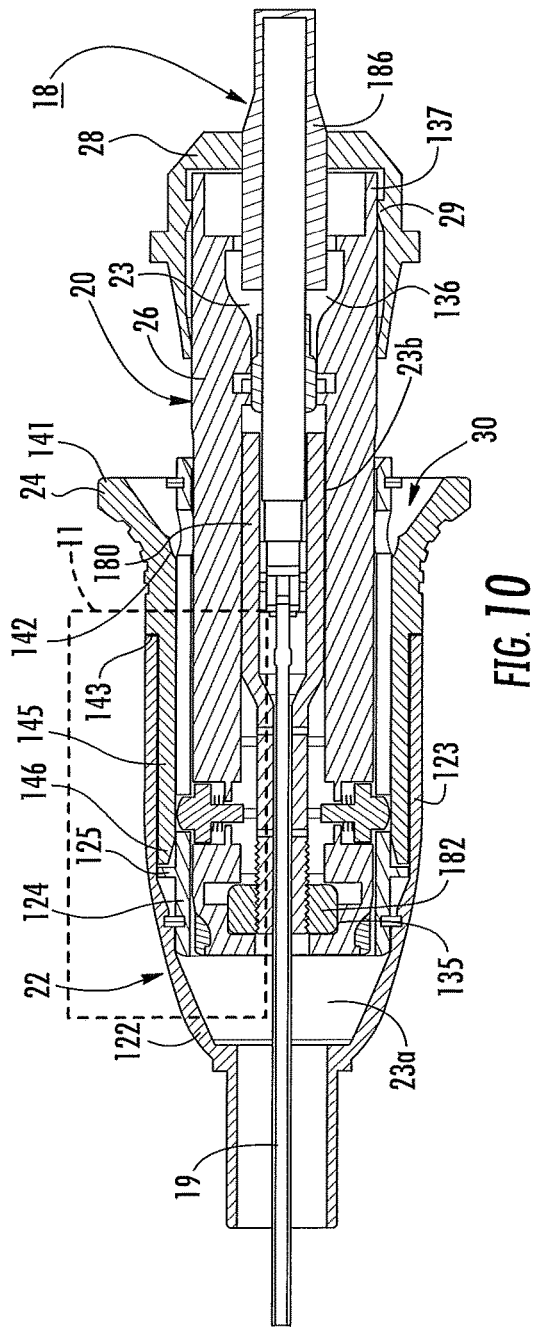
FIG. 10 is a longitudinal cross-sectional view of the retraction handle with the retraction control in the first position and the nose cone in the retracted position.
Figure 11:
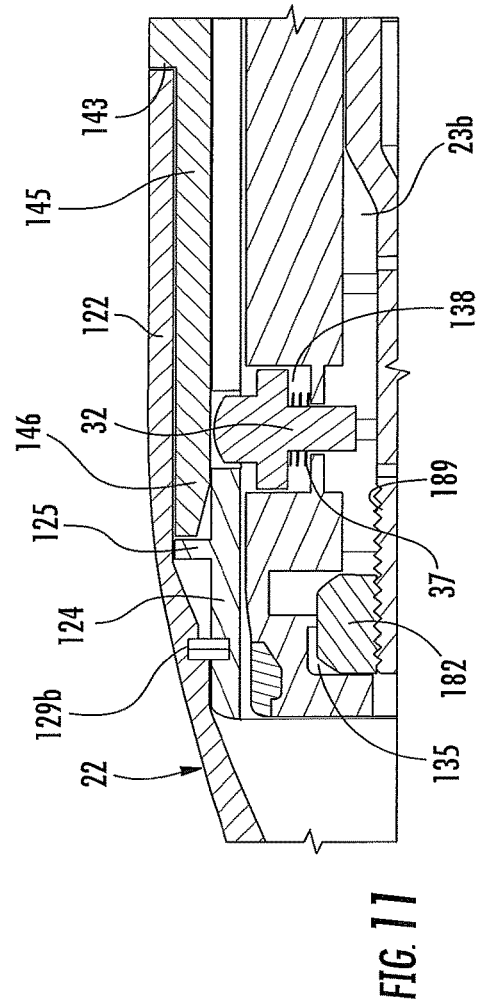
FIG. 11 is an enlarged view of the indicated area of detail of FIG. 10.

With particular reference to FIGS. 10 and 11, the nose cone 22 remains in the retracted position as the retraction control 24 is moved to the first position relative to the nose cone 22 to unlock the locking pins 32. When the retraction control 24 is moved from the second position to the first position, the ramp 146 of the distal finger 145 engages the locking surface 35 of the locking pins 32 to move the locking pins 32 against the pin biasing member 37 and towards the unlocked position. The distal finger 145 engages the control stop 125 to limit the distal translation of the retraction control 24 relative to the nose cone 22. Additionally or alternatively, the shoulder 143 of the proximal flange 141 may engage the proximal end of the outer wall 122 to limit the distal translation of the retraction control 24 relative to the nose cone 22.

Referring back to FIGS. 4 and 5, continued distal movement of the retraction control 24 moves the nose cone 22 distally relative to the housing body 26 to move the nose cone 22 to the extended position. The distal finger 145 may engage the control stop 125 or the shoulder 143 of the proximal flange 141 may engage the proximal end of the outer wall 122 to move the nose cone 22 to the extended position. As the nose cone 22 is extended, the retraction control 24 remains in the first position relative to the nose cone 22 and the locking surface 35 of the locking pins 32 slide along the inner surface of the sleeve 124 between the first and second openings 126, 128. When the nose cone 22 reaches the extended position, the locking surface 35 of the locking pins 32, being urged by the pin biasing members 37, extend through the first openings 126 such that the locking pins 32 are in the locked position to fix the nose cone 22 in the extended position.

With reference to FIGS. 1 and 14-18, the rail system 300 mounts to a bronchoscope (e.g., bronchoscope 11) to support instruments inserted through and associated with the bronchoscope (e.g., ablation catheter assembly 100). The rail system 300 is configured to separately support each instrument inserted through the bronchoscope and associated cabling, where necessary. While the rail system 300 detailed herein is described for use with a bronchoscope and associated instruments, it is contemplated that the support system may be used with other devices and associated instruments.

Figure 14:
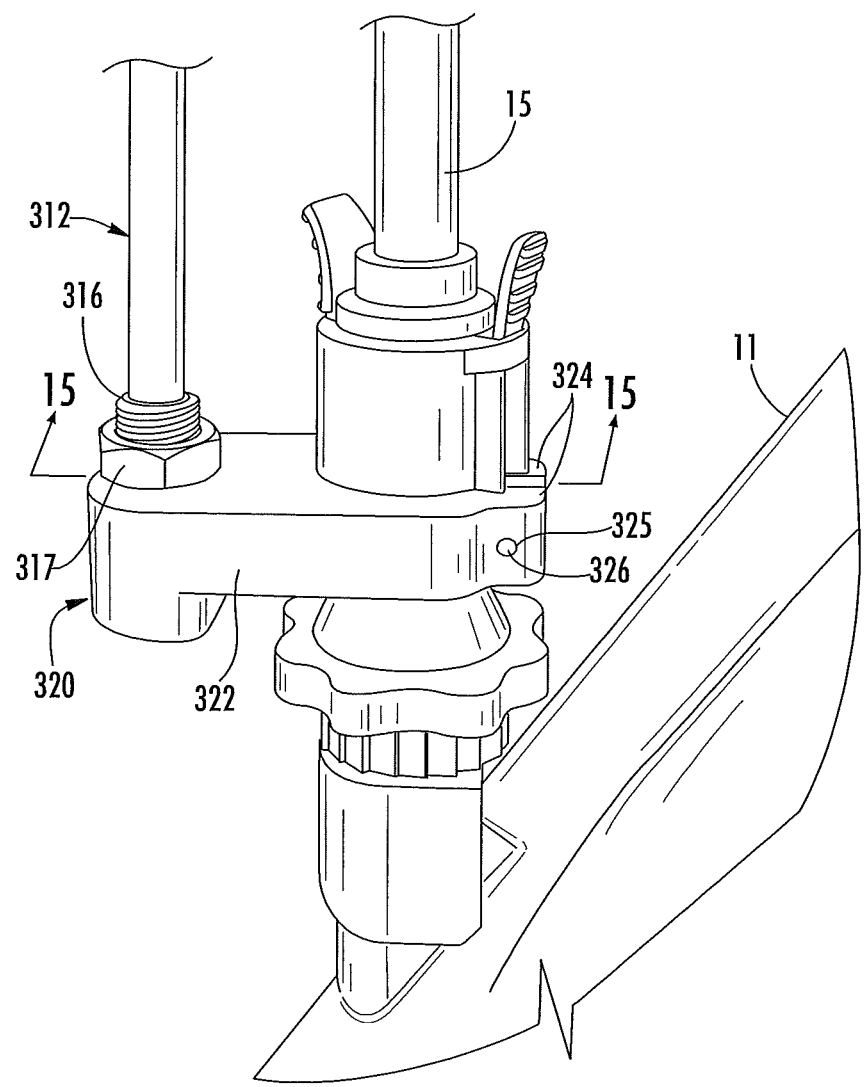
FIG. 14 is an enlarged view of the indicated area of detail of FIG. 1.
Figure 15:
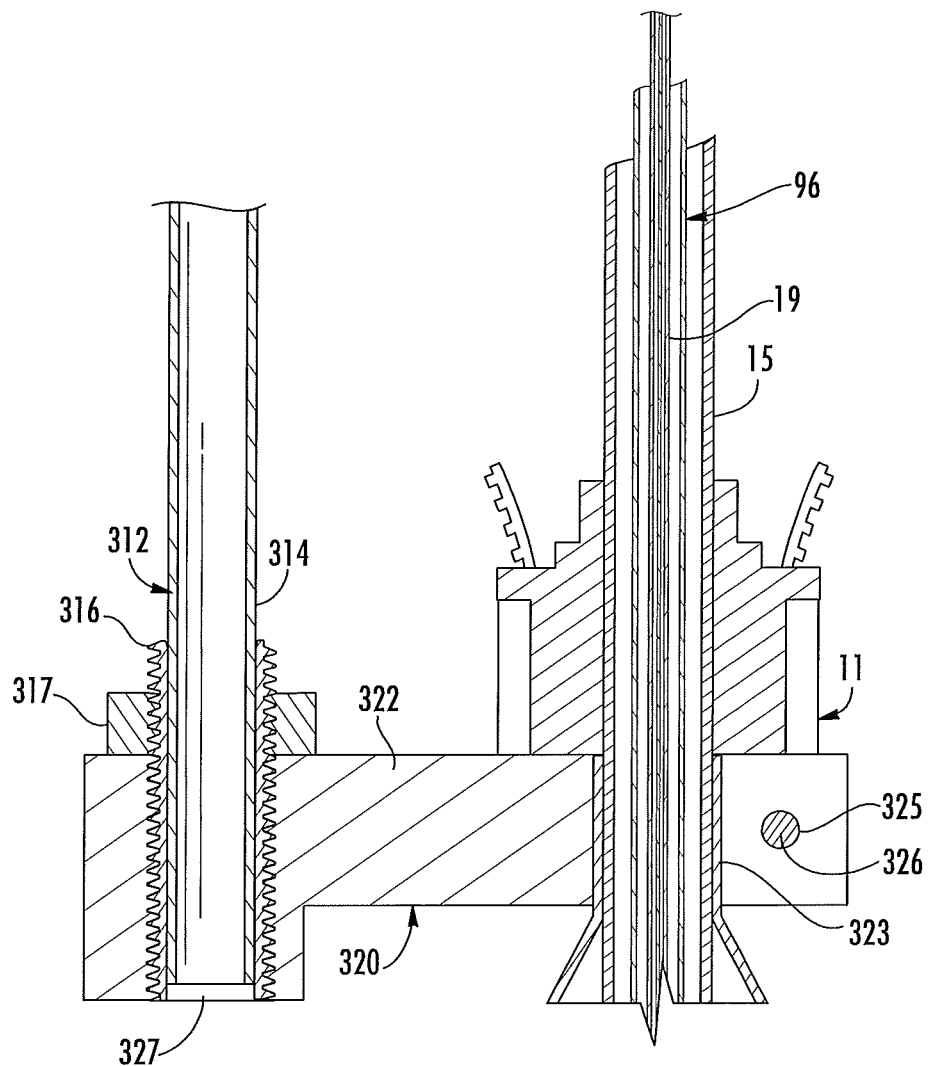

Referring now to FIGS. 1, 14, and 15, the rail system 300 includes a rail 312, a lower support 320, and a device support 330. The lower support 320 includes a support body 322 that mounts to a bronchoscope 11 to support the rail 312. The rail 312 has a lower end 316 and an upper end 318 and defines a longitudinal axis therebetween.

The support body 322 includes support fingers 324 and defines a rail opening 327 that is sized and configured to receive the lower end 314 of the rail 312. The support fingers 324 extend from the rail opening 327 in a direction orthogonal to the rail opening 327 and around a portion of the bronchoscope 11. The support fingers 324 define a support opening 323 therebetween that mates with the portion of the bronchoscope 11. Each support finger 324 defines a through locking hole 325 aligned with the locking hole of the other finger 324. A locking member 326 is inserted through the locking holes 325 to compress the support opening 323 about the portion of the bronchoscope 11 which secures the support body 322 to the bronchoscope 11. It is contemplated that the support opening 323 may compress about the telescopic EWC handle 15.

With reference to FIGS. 14 and 15, a collar 316 is disposed over the lower end 314 of the rail 312 and within the rail opening 327. The rail opening 327 and the collar 316 may be threadably coupled to one another. A thread portion of the collar 316 extends from the rail opening 327. A securement member 317 is threaded over the threaded portion of the collar 316 extending from the rail opening 327. The securement member 317 radially compresses the collar 316 against the rail 312 to secure the rail 312 within the rail opening 317. It is also contemplated that the distal end 314 of the rail 312 may be threaded and configured to thread directly into the lower support 320 without the collar 316. In such embodiments, the securement member 317 may be a lock nut to The rail 312 extends vertically from the lower support 320 towards the upper end 318. The rail 312 may be fully supported by the lower support 320 or a support (not shown) may be releasably coupled adjacent the upper end 318 to provide additional support to the rail 312. The rail 312 may be constructed of any suitable material including, but not limited to, surgical steel, fiberglass, and, plastic.

Figure 16:
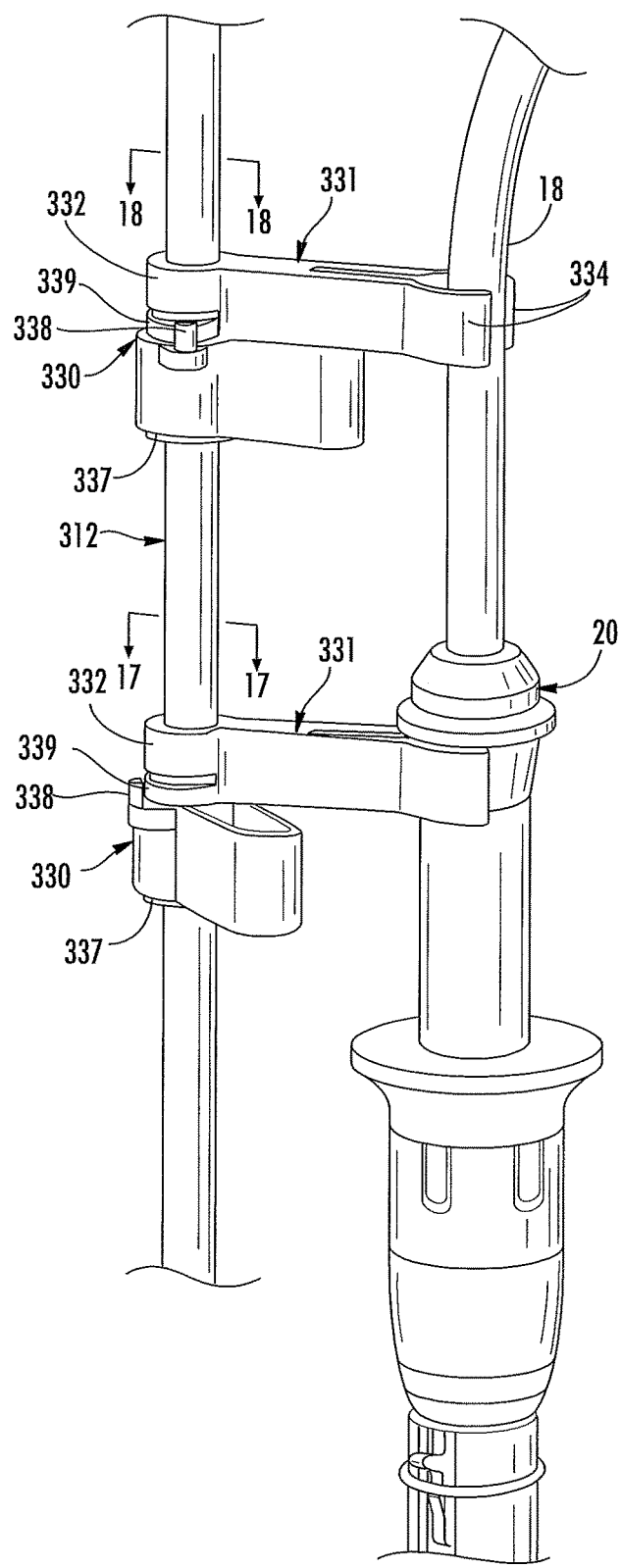
FIG. 16 is an enlarged view of the indicated area of detail of FIG. 1.
Figures 17, 18:
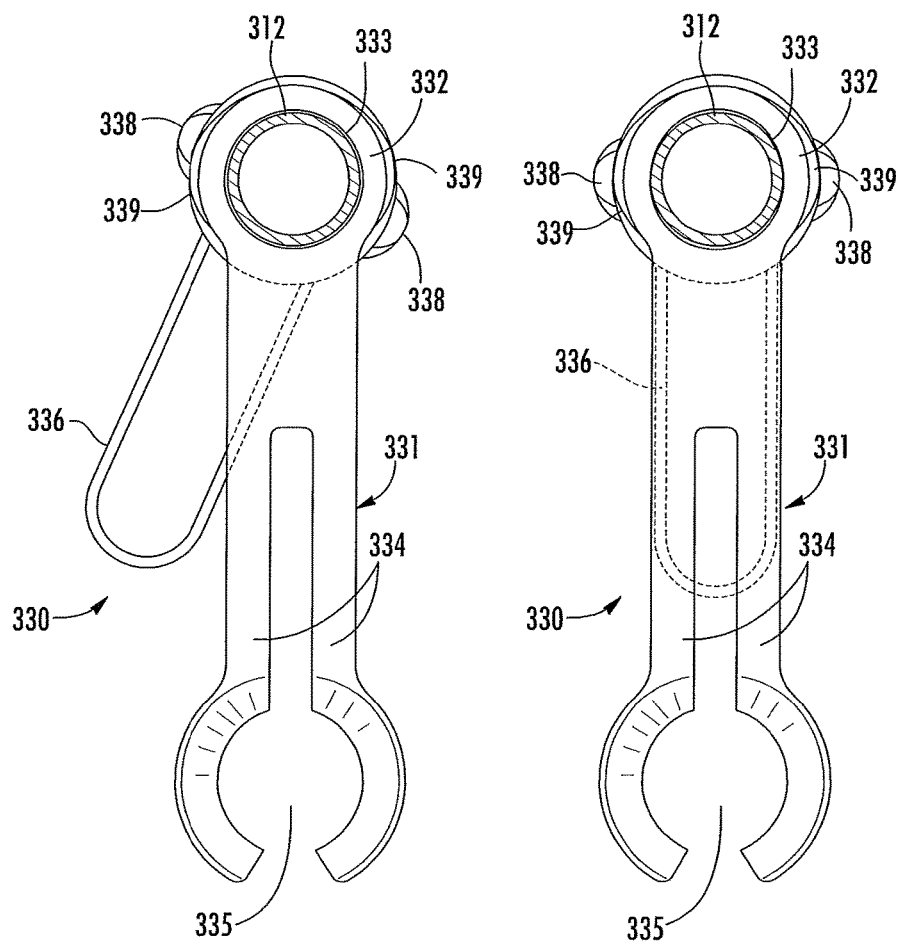
FIG. 17 is a top view of a device support taken along the line 17-17 FIG. 16 illustrating a locking arm in an unlocked position.
FIG. 18 is a top view of a device support taken along the line 18-18 of FIG. 16 illustrating a locking arm in a locked position.

Referring to FIGS. 16-18, one or more device supports 330 are positioned along the rail 312 and configured to support instruments (e g, handle 20, cable 18 of ablation catheter 100) inserted through the bronchoscope 11. The device support 330 includes a clamp arm 331 having a clamp arm collar 332, which defines a rail passage 333 therethrough. The clamp arm collar 332 is sized and configured to slide over the rail 312 in an unlocked configuration and to engage the rail 312 in a locked configuration to fix the device support 330 in position along the rail 312. In the unlocked configuration the rail passage 333 is sized and configured to freely slide over the rail 312 and in the locked configuration the rail passage 333 is sized and configured to engage the rail 312. In the locked configuration, the device support 330 may be longitudinally and/or radially fixed to the rail 312.

The device support 330 includes instrument fingers 334 extending from the clamp arm collar 332 in a direction orthogonal to the longitudinal axis of the rail 312. The instrument fingers 334 define an instrument passage 335 therebetween that is sized and configured to releasably couple to and to support an instrument (e.g., handle 20, ablation catheter assembly 18).

The device support 330 further includes a locking arm 336 that transitions the clamp arm collar 332 between the locked and unlocked configurations. The locking arm 336 includes a locking arm collar 337 that is disposed over a portion of the clamp arm collar 332 and includes a locking cam 338. The locking cam 338 extends from the locking arm collar 337 substantially parallel to the longitudinal axis of the rail 312 and towards the clamp arm 331. A portion of the clamp arm collar 332 includes a radial camming surface 339. The camming surface 339 forms a radial ramp such that as the locking arm 336 is rotated from an unlocked position (FIG. 17) towards a locked position (FIG. 18), the locking cam 338 engages the camming surface 339 to compress the clamp arm collar 332 towards the locked position. The locking cam 337 may engage the clamp arm 331 in one of the locked or unlocked positions of the locking arm 336 to prevent the locking arm 36 from excessive rotation about the clamp arm collar 332 and to provide indicia (e.g., tactile, visual, or audible indicia) that the device support 330 is in the locked or unlocked position.

In embodiments, the locking arm collar 337 may include two locking cams 338 radially disposed about the locking arm collar 337 about 180° apart as shown in FIGS. 17 and 18. One of the locking cams 337 may engage the clamp arm 331 in the locked configuration and the other of the locking cams may engage the clamp arm 331 in the unlocked configuration to prevent the locking arm 336 from excessive rotation about the clamp arm collar 332 and to provide indicia (e.g., tactile, visual, or audible indicia) that the device support 330 is in the locked and unlocked configuration.

In use, the support fingers 324 of the lower support are slid over a portion of the bronchoscope 11 such that the portion of the bronchoscope 11 is positioned within the opening 323. A locking member 326 is inserted through the locking holes 325 of the support fingers 324 and tightened to lock the lower support 320 to the bronchoscope 11.

The lower end 314 of the rail 312 is inserted into the rail opening 327 defined in the lower support 320. The lower end 314 may be inserted into the collar 316 disposed within the rail opening 327. The securement member 317 is tightened over the threaded portion of the collar 316 to secure the rail 312 to the lower support 320. The upper end 318 of the rail 312 may be coupled to a support (not shown) to provide additional support to the bronchoscope 11. It is contemplated that the support may be a support stand supported on from the floor, a support hanging from a ceiling, or a support extending from a wall.

A catheter (e.g., ablation catheter assembly 100) is then inserted through the telescopic EWC handle 15 and the EWC 96. A proximal end of the ablation catheter assembly 100 may include a catheter collar (not shown) positioned on the outer surface of the cable 18 for engagement with a device support 330 or the device support 330 may clamp directly to an outer surface of the cable 18, as shown.

A first device support 330 is positioned along the rail 312 such that the instrument passage 335 of the first device support 330 is adjacent a portion of ablation catheter assembly 100 (e.g., the catheter collar or the cable 18). The portion of the ablation catheter assembly 100 is then coupled to the clamp arm 332 by urging the portion of ablation catheter assembly 100 into the instrument passage 335. The first device support 330 is then locked in position on the rail 312 by moving the lock arm 336 of the first device support 330 to the locked position. When the portion of the ablation catheter assembly 100 is secured within the instrument passage 335 with the device support 330 in the locked configuration, the portion of the ablation catheter assembly 100 is supported by the first device support 330. It is contemplated that the first device support 330 may be locked prior to urging the portion of the ablation catheter assembly 100 into the instrument passage 435.

Figure 19:
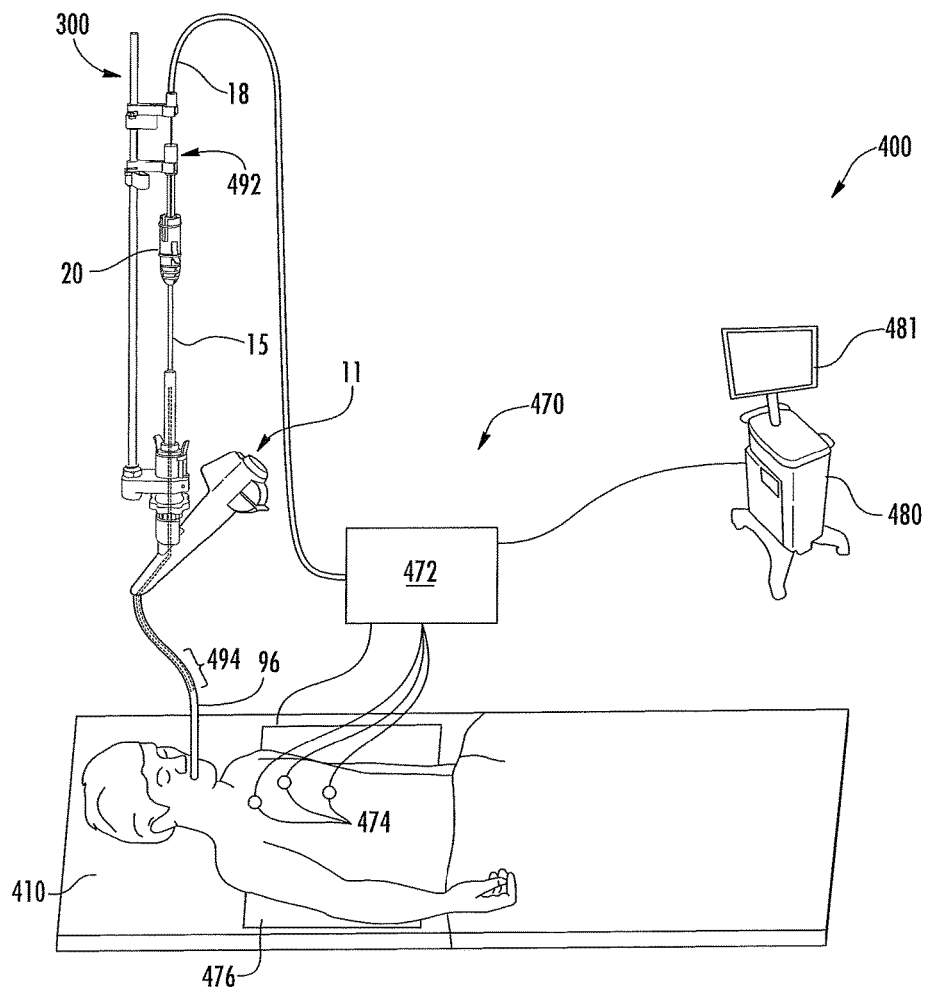
FIG. 19 is a perspective view of the surgical system of FIG. 1 in use with an electromagnetic navigation system 400 provided in accordance with the present disclosure.

With reference to FIG. 19, an electromagnetic navigation (EMN) system 400 is provided in accordance with the present disclosure. FIG. 19 also depicts the ablation catheter assembly 100, the cable 18 (which connects on one end to a microwave generator (not shown) and on the other end to) the handle 20, and the rail system 300 of FIG. 1 for use with the EMN system 400. One such EMN system is the ELECTROMAGNETIC NAVIGATION BRONCHOSCOPY® system currently sold by Covidien LP. Among other tasks that may be performed using the EMN system 400 are planning a pathway to target tissue, navigating a catheter guide assembly to the target tissue, deploying an instrument adjacent or into the target tissue to treat or capture the target tissue, digitally marking the location of the target tissue in a data file related to the planned pathway, and placing one or more echogenic markers at or around the target tissue.

The EMN system 400 generally includes an operating table 410 configured to support a patient; the bronchoscope 11 configured for insertion through the patient's mouth and/or nose into the patient's airways; a tracking system 470 including a tracking module 472, a plurality of reference sensors 474, and an electromagnetic field generator 476; and a workstation 480 including software and/or hardware used to facilitate pathway planning, identification of target tissue, navigation to target tissue, and digitally marking the biopsy location.

Before an ablation procedure can be performed, a locatable guide (LG) catheter 492, including an electromagnetic (EM) sensor 494, is inserted into the telescopic handle 15, and connected to rail system 300. Upon insertion into the telescopic EWC handle 15, the LG catheter 492 enters the EWC 96 and is locked into position such that the sensor 494 is positioned slightly beyond the distal end 96a of the EWC 96 during placement of the EWC 96. The location of the EM sensor 494, and thus the distal end 96a of the EWC 96, within an electromagnetic field generated by the electromagnetic field generator 476 can be derived by the tracking module 472, and the workstation 480. During insertion and placement of the distal end 96a of the EWC 96, the telescopic EWC handle 15 and the LG catheter 492 inserted therein can be manipulated by rotation and compression to steer and position the LG catheter 492. An example of a similar catheter guide assembly is currently marketed and sold by Covidien LP under the name EDGE™ Procedure Kits. For a more detailed description of the use of the catheter guide assembly reference is made to commonly-owned U.S. Provisional Patent Application Ser. No. 62/020, 240 filed on Jul. 2, 2014 and entitled System and Method for Navigating within the Lung, the entire contents of which are hereby incorporated by reference.

Once the LG catheter 492 and EM Sensor 494 are navigated to a target within the patient, the LG catheter 492 is removed from the EWC 96, bronchoscope 11, and telescopic EWC handle 15, and an ablation catheter system 100 may be inserted to treat the tissue at the target. When the EWC 96 is positioned, the bronchoscope 11 is held steady as the LG catheter 492 and the EM sensor 494 are withdrawn from the EWC 96 and the ablation catheter assembly 100 is inserted through the EWC 96 until the distal end 19a of the ablation probe 19 is adjacent the distal end of the EWC 96. In this configuration the ablation catheter assembly 100, handle 20, and rail system 300 have substantially the orientation depicted in FIG. 1. The handle 20 is then manipulated to retract and extend the EWC 96 as detailed above to permit the clinician to treat the target. The ablation catheter assembly 100 is then withdrawn from the EWC 96 permitting additional instruments to be inserted through the EWC 96, the EWC 96 to be relocated to another target, or the EWC 96 to be removed from the airway of the patient.

In one embodiment, the EM sensor 494 may be disposed on a distal end 19a the ablation probe 19. During insertion and positioning of the ablation probe 19 and EM sensor 494, the handle 20 is in the extended position (FIG. 4) such that the distal end 19a of the ablation probe 19 is substantially within the EWC 96 as shown in FIG. 12. In addition, ablation probe 19 and the handle 20 may be secured to the bronchoscope 11 with the rail system 300, as detailed above, such that as a clinician manipulates the telescopic EWC handle 15, the ablation probe 19c and the handle 20 move in concert together with the telescopic EWC handle 15 permitting one-handed manipulation of the bronchoscope 11, the telescopic EWC handle 15, the ablation catheter assembly 18, and the handle 20.

When the EM sensor 494 is positioned adjacent the target, the handle 20 is moved to the retracted position (FIG. 10) to retract the EWC 96 such that the distal end 19a of the ablation probe 19 is exposed as shown in FIG. 13. With the distal end 19a of the ablation probe 19 exposed, the ablation probe 19 may be activated to treat the target. After the target is treated, the handle 20 is returned to the extended position such that the distal end 19a of the ablation probe 19 is substantially within the EWC 96 (FIG. 12). The ablation catheter assembly 100 may then be removed from the EWC 96 leaving the distal end of the EWC 96 adjacent the target. Additional instruments may then be passed through the EWC 96 to treat the target, the EWC 96 may be relocated to another target, or the EWC 96 may also be removed from the airway of the patient.

Figure 20A:
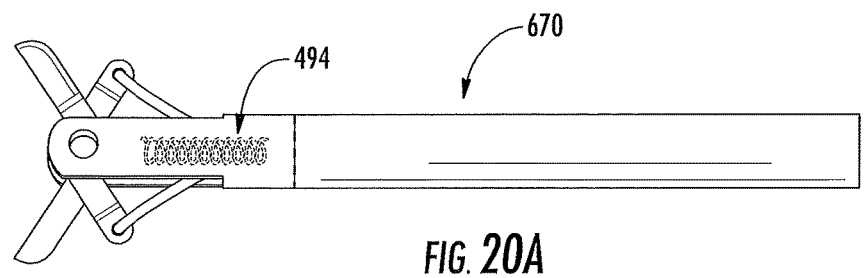
FIGS. 20A-20C are side views of distal ends of instruments that may be used with the surgical system of FIG. 1
Figure 20B:
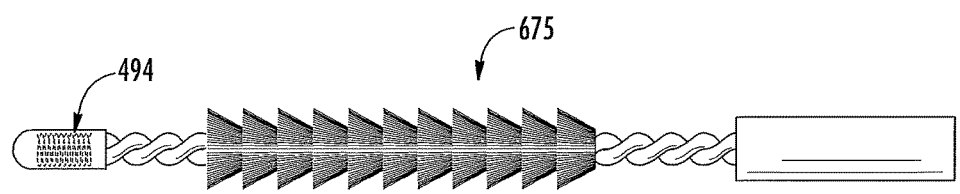
Figure 20C:
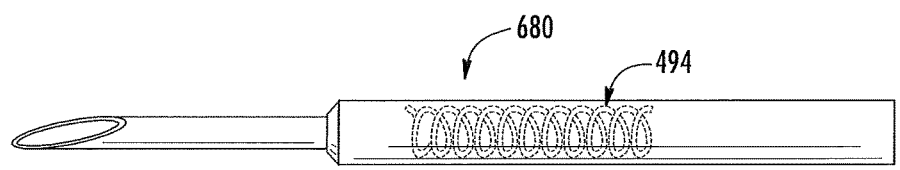
Figure 22:
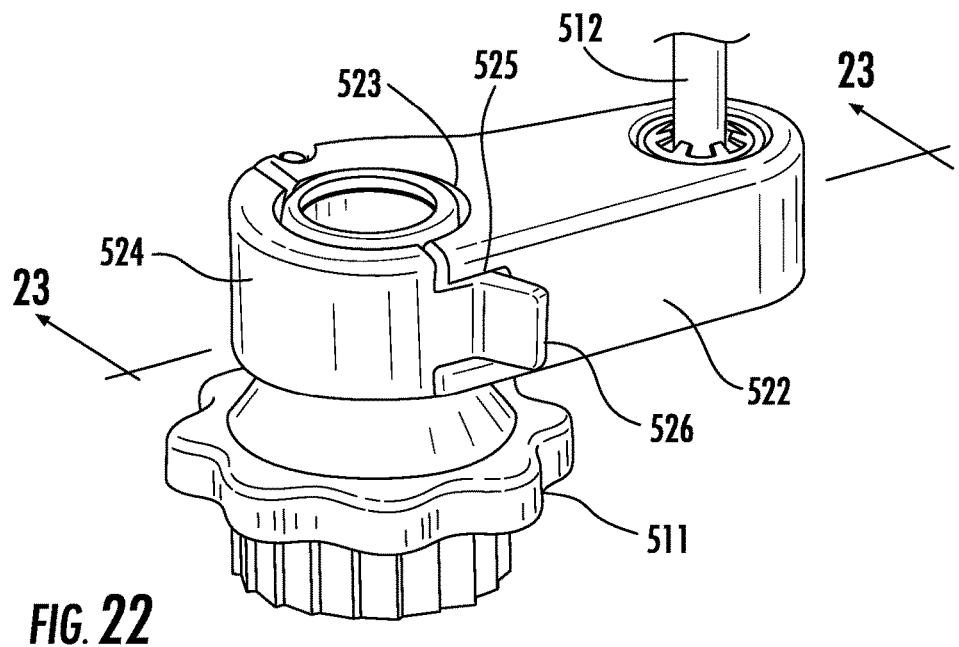
FIG. 22 is an enlarge perspective view of the area of detail indicated in FIG. 21.
Figure 23:
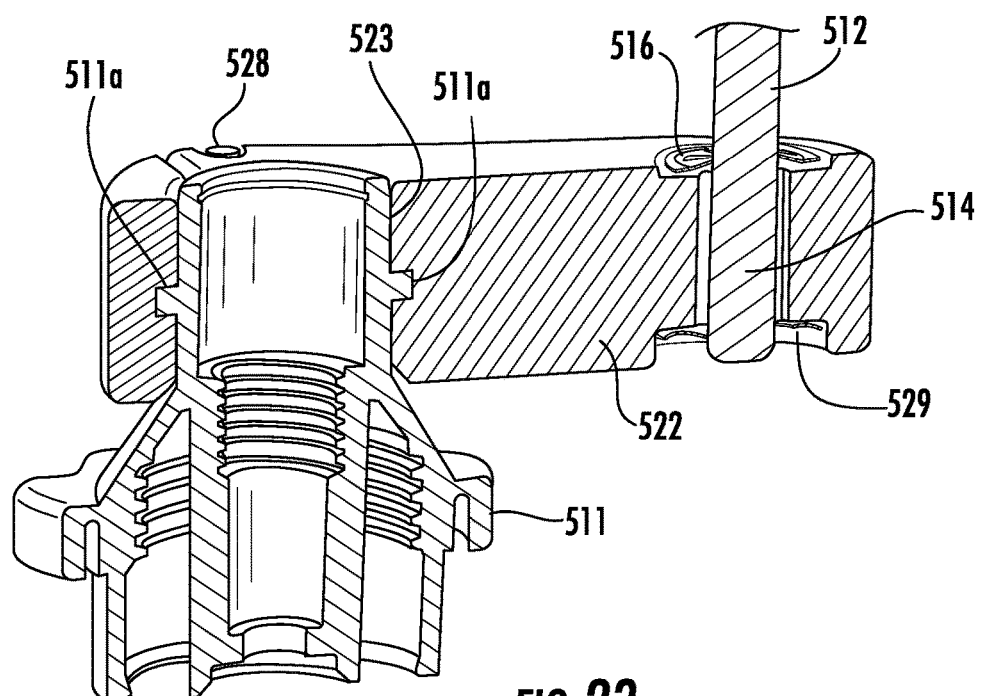
FIG. 23 is a cross-sectional view taken along the section line 23-23 of FIG. 22.

As described above, the rail system 300 and EMN system 400 may be used in combination with an LG catheter 492 or an ablation catheter 100. However, other instruments may also benefit from the rail system 300. Examples of additional instruments that may be inserted through the EWC 96 to treat and/or sample the target are shown in FIGS. 20A-20C, depicting biopsy forceps 670, a biopsy brush 675, and a biopsy needle 680. As shown in FIG. 20, each instrument includes an EM sensor 494 disposed thereon in accordance with the present disclosure, however, instruments without EM sensors 494 may also be employed without departing from the scope of the present disclosure. A proximal end of the instruments 670, 675, 680 may include a handle 20 similar in construction to what is shown in FIGS. 1-11, enabling the retraction and extension of the EWC 96.

Referring to FIGS. 21-27, another rail system 500 is provided in accordance with the present disclosure and includes a rail 512, a lower support 520, and a device support 530. The rail system 500 is similar in structure and function to the rail system 300 detailed above, as such only the differences will be detailed herein for reasons of brevity. The lower support 520 includes a support body 522 that is coupled to a lower or distal end 514 of the rail 512 and defines a rail opening 529 (FIG. 23) that receives the lower end of the rail 512 therein. The lower support 520 may include a collar 516 positioned in or adjacent to the rail opening 529 that engages an outer surface of the rail 512 to secure the lower support 520 to the rail 512.

Figure 24:
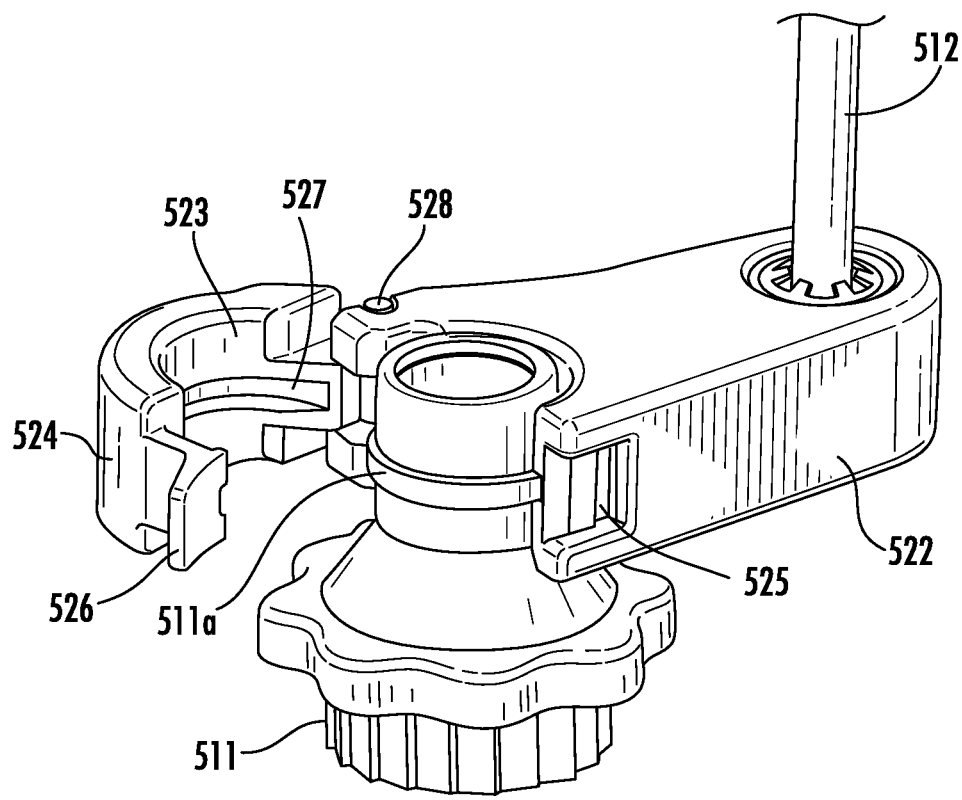
FIG. 24 is a perspective view of the lower support of FIG. 22 with the support arm in an open configuration positioned about a portion of a bronchoscope.
Figure 25:
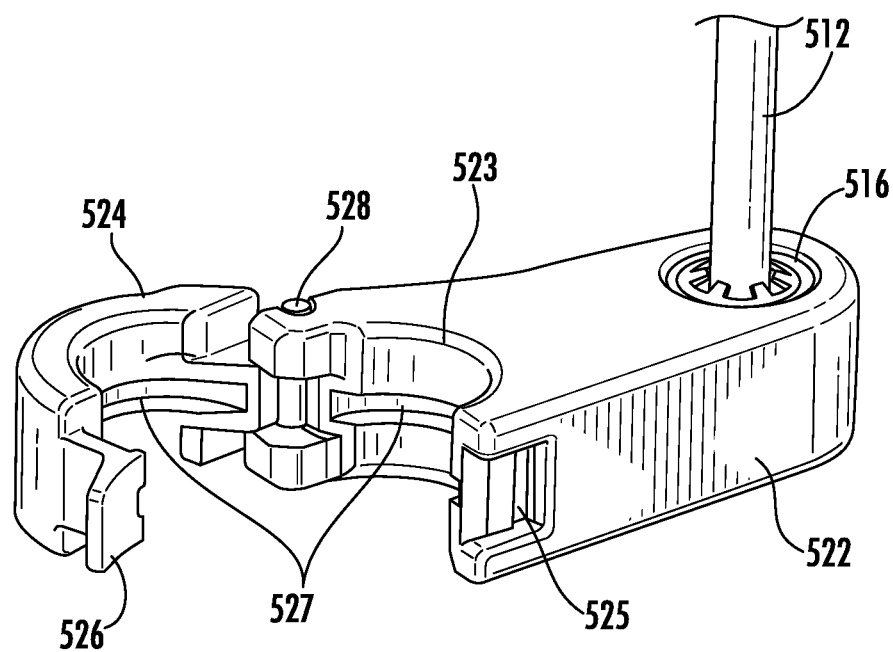
FIG. 25 is a perspective view of the lower support of FIG. 24 with the portion of the bronchoscope removed.

The support body 522 of the lower support 520 extends from the rail opening 529 to a support arm 524 that has a clamped configuration (FIGS. 22 and 23) and an open configuration (FIGS. 24 and 25). The support arm 524 and the support body 522 define a support opening 523 that is configured to receive and clamp to a bronchoscope 11 (FIG. 1) using a bronchoscope adapter 511 to secure the lower support 520 to the bronchoscope 11. The bronchoscope adapter 511 may be threaded to a working channel port on the bronchoscope 11 as is known in the art. The support arm 524 pivots about a pivot pin 528 to transition between the clamped and open configurations thereof. The support arm 524 includes a clip 526 and the support body 522 defines a clip detent 525 (FIG. 25) that is configured to selectively receive the clip 526 to secure the support arm 524 in the clamped configuration. The clip 526 may provide tactile feedback when the clip 526 is secured in the clip detent 525. The bronchoscope adapter 511 may include an annular ring 511a and the inner surface of the support opening 523 may define an annular groove 527 that is sized to receive the annular ring 511a to longitudinally fix the lower support 520 to the bronchoscope adapter 511 when the support arm 524 is in the clamped configuration. It is contemplated that the cooperation of the annular ring 511a and the annular groove 527 may assist in aligning the lower support 520 with the bronchoscope 11 (FIG. 1).

It is also contemplated that the annular ring 511a and the annular groove 527 may only be defined along a portion of the support opening 23. In such embodiments, the cooperation of the annular ring 511a and the annular groove 527 may radially fix the lower support 520 to the bronchoscope adapter 511.

Figure 26:
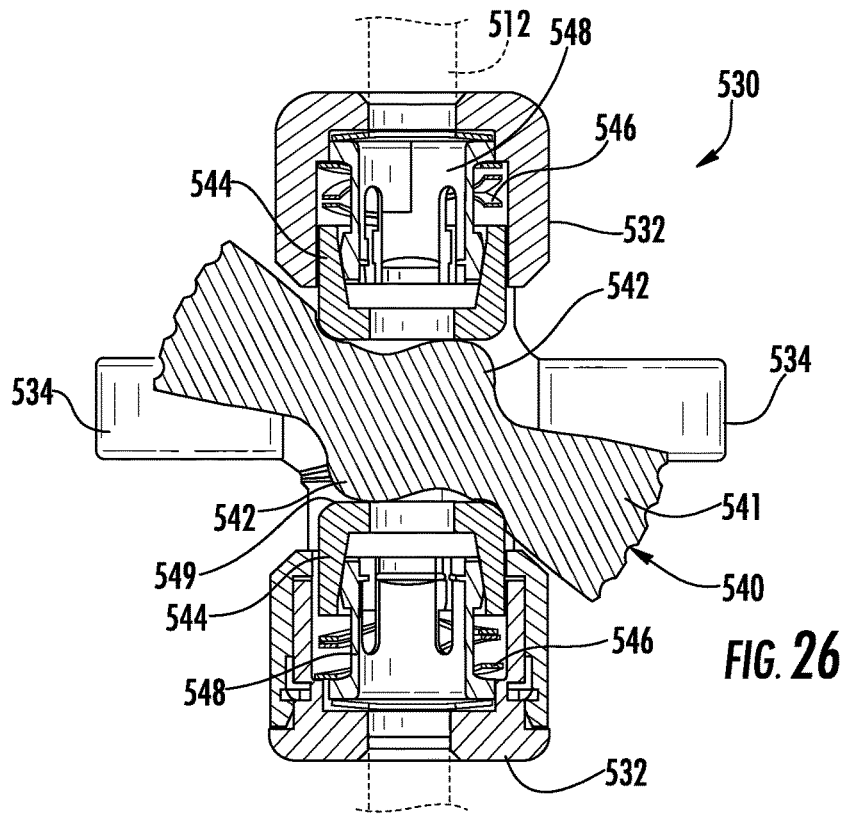
FIG. 26 is a cross-sectional view taken along the section line 26-26 of FIG. 21 illustrating the instrument support in an unlocked configuration.
Figure 27:
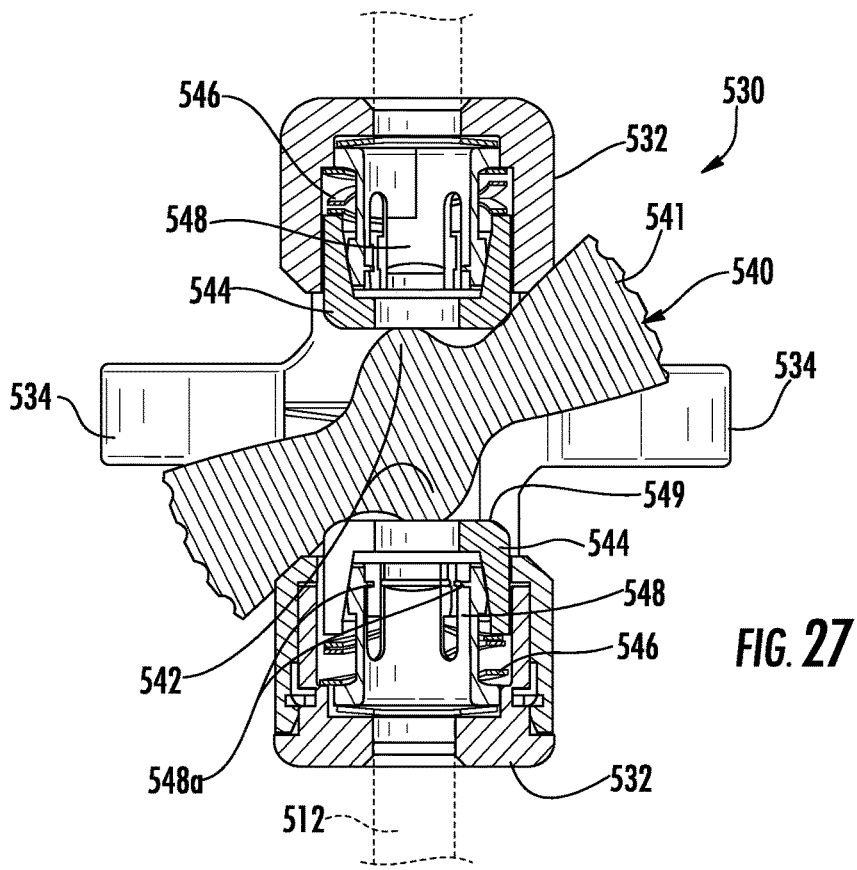
FIG. 27 is a cross-sectional view of the instrument support of FIG. 27 in a locked configuration.

With particular reference to FIGS. 26 and 27, the device support 530 includes a support collar 532 slidably disposed over the rail 512, instrument fingers 534 extending therefrom, and a locking mechanism 540 disposed therein. The locking mechanism 540 includes a locking arm 541 having locking cams 542. The locking arm 541 is pivoted between an unlocked position (FIG. 26) and a locked position (FIG. 27) to actuate the locking mechanism 540 between an unlocked configuration and a locked configuration. It will be appreciated that the locking arm 541 includes a passage that permits support collar 532 and the locking mechanism 540 to slide on the rail without engaging the rail 512 when the locking arm 541 is in the unlocked position. As shown, the locking mechanism 540 has upper and lower mechanisms that are substantially similar to one another and function in concert with one another; however, it is contemplated the locking mechanism 540 may only include either the upper or lower mechanism or that the each of the upper and lower mechanisms may be independently actuated.

The locking mechanism 540 further includes an outer member 544 and an inner member 548 coaxially positioned with one another about the rail 512. The outer member 544 and the inner member 548 are moveable relative to one another between an unlocked position (FIG. 26) and a locked position (FIG. 27). The outer member 544 may be biased towards the unlocked position by a biasing member 546. The outer member 544 includes a camming surface 549 that is engaged by the locking cam 542 of the locking arm 541.

To fix the device support 530 to the rail 512, the locking arm 541 is pivoted from the unlocked position (FIG. 26) to a locked position (FIG. 27). As the locking arm 541 is pivoted, the locking cams 542 cam the outer member 544 against the biasing member 546 and over the inner member 548 such that inner angled surfaces of the outer member 544 engage outer angled surfaces of the inner member 548 such that the inner member 548 is radially compressed into the rail 512 to engage the rail 512. It is contemplated that the inner member 548 may include teeth 548a that engage the rail 512 to fix the inner member 548 to the rail 512. The inner member 548 is coupled to the support collar 532 such that when the inner member 548 is fixed to the rail 512, the support collar 532 and thus the device support 530 is fixed to the rail 512. It is contemplated that the inner member 548 may be integrally formed with the support collar 532.

Figure 28:
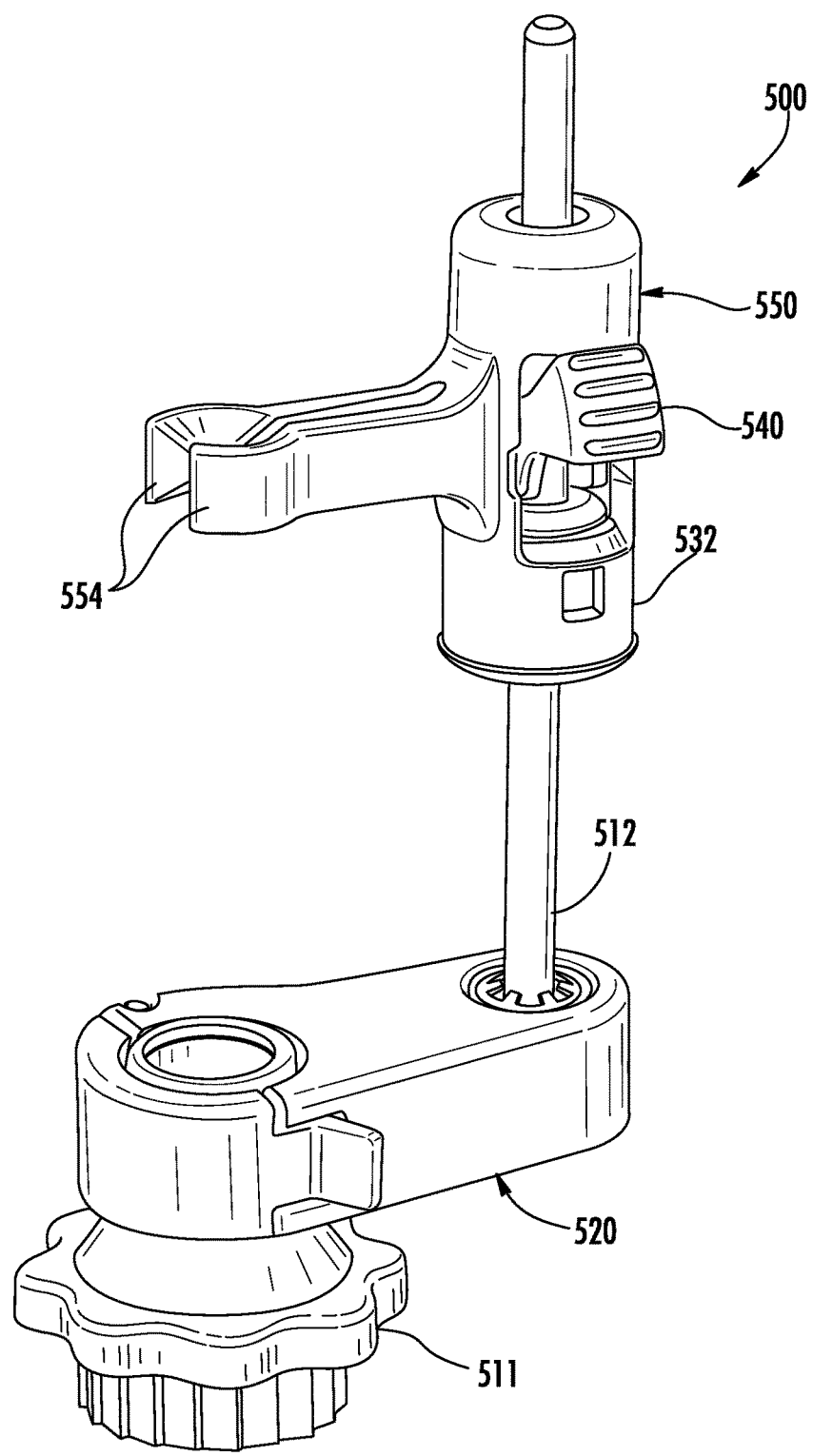
FIG. 28 is a perspective view of the rail system of FIG. 21 with another instrument support provided in accordance with the present disclosure.

As described above, the rail system 500 may include device support 530. However, other device supports may be used in combination with the rail system 500 which are configured to support a variety of instruments inserted through he EWC 96. For example, as shown in FIG. 28 an additional device support 550 is illustrated in use with rail system 500. The device support 550 includes a support collar 532 and instrument fingers 554 extending therefrom. The instrument fingers 554 are substantially similar to the instrument fingers 354 detailed above with respect to device support 330.

While the use of the handle 20 and the rail system 300, 500 are detailed herein for use in the airway of a patient, it is contemplated that the handle 20 and/or the rail system 300 may be used in a variety of surgical procedures utilizing elongated surgical instruments with extended working channels. For example, the handle 20 and or rail system 300, 500 may be used to stabilize a guide wire or catheter during various endovascular procedures such as cardiac interventions, general vascular interventional procedures, cerebral interventions, etc. These procedures may include, but are not limited to, balloon dilations, stent placements, percutaneous valve replacement, percutaneous valve repair, pacing lead placement, cardiac ablation procedures, and electrical mapping procedures.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. A handle for longitudinal movement of a first tubular member over a second tubular member, the handle comprising:
    a handle body;
    a nose cone having a sleeve and an outer wall defining a control channel therebetween, the nose cone moveable over the handle body between an extended position and a retracted position;
    a locking mechanism including a locking pin having a retention plate, the locking pin being biased out of the slot defined in the handle body such that the retention plate retains the locking pin within the slot, the locking mechanism being disposed within a slot defined in the handle body and having a locked position and an unlocked position for selectively fixing the nose cone in the extended and retracted positions; and
    a retraction control including a finger positioned within the control channel of the nose cone, the retraction control having first and second positions relative to the nose cone for transitioning the locking mechanism between the locked and unlocked positions and for moving the nose cone between the extended and retracted positions.

2. The handle of claim 1, wherein when the nose cone is in the extended position and the retraction control is in the first position, the locking mechanism is in the locked position to fix the nose cone in the extended position.

3. The handle of claim 1, wherein when the nose cone is in the extended position and the retraction control is in the second position, the locking mechanism is in the unlocked position such that the nose cone is moveable relative to the handle body.

4. The handle of claim 3, wherein when the nose cone reaches the retracted position, the locking mechanism transitions to the locked position to fix the nose cone in the retracted position.

5. The handle of claim 1, wherein when the nose cone is in the retracted position and the retraction control is in the second position, the locking mechanism is in the locked position to fix the nose cone in the extended position.

6. The handle of claim 1, wherein when the nose cone is in the retracted position and the retraction control is in the first position, the locking mechanism is in the unlocked position such that the nose cone is moveable relative to the handle body.

7. The handle of claim 6, wherein when the nose cone reaches the extended position, the locking mechanism transitions to the locked position to fix the nose cone in the extended position.

8. The handle of claim 1, wherein the second position of the retraction control is proximal to the first position of the retraction control.

9. The handle of claim 1, wherein the sleeve of the nose cone defines first and second openings, wherein when the nose cone is in the extended position and the locking pin is in the locked position, the locking pin is disposed within the first opening, and wherein when the nose cone is in the retracted position and the locking pin is in the locked position, the locking pin is disposed within the second opening.

10. A surgical system comprising:
    an extended working channel having proximal and distal ends;
    a handle defining a through passage, the handle including:
        an adjustment nut;
        a housing body defining a proximal portion of the through passage, the housing body defining a nut recess for receiving the adjustment nut to longitudinally fix the ablation probe to the housing body;
        a nose cone coupled to the proximal end of the extended working channel and having a sleeve and an outer wall defining a control channel therebetween, the nose cone defining a distal portion of the through passage in communication with the extended working channel, the nose cone longitudinally moveable over the housing body between an extended position and a retracted position; and
        a locking mechanism having a locked position and an unlocked position for selectively fixing the nose cone in the extended and retracted positions; a retraction control including a finger positioned within the control channel of the nose cone, the retraction control having first and second positions relative to the nose cone for transitioning the locking mechanism between the locked and unlocked positions and for moving the nose cone between the extended and retracted positions; and a catheter assembly disposed within the through passage of the handle, the catheter assembly including:
        a catheter hub positioned in the proximal portion of the through passage, the catheter hub having the adjustment nut positioned over an outer surface of the catheter hub; and
        an ablation probe extending from the catheter hub through the nose cone of the handle and through the extended working channel, the ablation probe having a distal end that is disposed within the extended working channel when the handle is in the extended position and that is positioned distal to the distal end of the extended working channel when the handle is in the retracted position.

11. The system of claim 10, wherein the catheter hub combines coolant tubes and an antenna into the ablation probe.

12. The system of claim 10, wherein the adjustment nut is threaded to cooperate with threads on the outer surface of the catheter hub to allow fine adjustment of the length of the ablation probe relative to the housing body.

13. The system of claim 11, wherein a distal end of the ablation probe is positioned within the distal end of the extended working channel when the nose cone is in the extended position, and wherein the distal end of the ablation probe is positioned distal to the distal end of the extended working channel when the nose cone is in the retracted position.

14. A method of assembling a surgical system, the method comprising:
  positioning a catheter assembly within a half of a first portion of a passage defined within a first half of a housing body of a handle wherein an adjustment nut is positioned within a nut recess defined in the housing body to adjust the length of the probe extending distally from the housing body;
  securing a second half of the housing body of the handle to the first half of the housing body with the catheter assembly positioned in a half of the first portion of the passage defined within the second half of the housing body to form the housing body;
  sliding a nose cone of the handle over a distal portion of the housing body, the nose cone defining a second portion of the passage that receives a probe of the catheter assembly therethrough; and
  inserting a finger of a retraction control within a control channel defined between a sleeve and outer wall of the nose cone.

15. The method of claim 14, further including rotating the adjustment nut about a threaded portion of the catheter hub to fix the length of the probe extending distally from the housing body.

16. The method of claim 14, wherein securing the second half of the housing body to the first half of the housing body prevents adjustment of the length of the probe extending distally from the housing body during use of the surgical system.

* * * * *